(12) United States Patent
Shimizu

(10) Patent No.: US 11,884,617 B2
(45) Date of Patent: Jan. 30, 2024

(54) METHOD FOR PRODUCING ACETIC ACID

(71) Applicant: DAICEL CORPORATION, Osaka (JP)

(72) Inventor: Masahiko Shimizu, Himeji (JP)

(73) Assignee: DAICEL CORPORATION, Osaka (JP)

( * ) Notice: Subject to any disclaimer, the term of this patent is extended or adjusted under 35 U.S.C. 154(b) by 573 days.

(21) Appl. No.: 16/482,464

(22) PCT Filed: Jul. 2, 2018

(86) PCT No.: PCT/JP2018/025077
§ 371 (c)(1),
(2) Date: Jul. 31, 2019

(87) PCT Pub. No.: WO2020/008506
PCT Pub. Date: Jan. 9, 2020

(65) Prior Publication Data
US 2021/0331996 A1    Oct. 28, 2021

(51) Int. Cl.
*C07C 51/12* (2006.01)
*B01J 19/18* (2006.01)
(Continued)

(52) U.S. Cl.
CPC ........... *C07C 51/12* (2013.01); *B01J 19/1856* (2013.01); *B01J 31/20* (2013.01); *C07C 51/44* (2013.01);
(Continued)

(58) Field of Classification Search
CPC ......... C07C 51/12; C07C 51/44; C07C 53/08; B01J 31/20; B01J 19/1856;
(Continued)

(56) References Cited

U.S. PATENT DOCUMENTS 9,776,941 B2    10/2017  Shimizu et al.
2008/0021179 A1*  1/2008  Mul .......................... C07C 2/32
                                                                    526/90
(Continued)

FOREIGN PATENT DOCUMENTS

EP        3 330 248 A1    6/2018
EP        3 333 147 A1    6/2018
(Continued)

OTHER PUBLICATIONS

Chemspeed (pp. 1-6, Published Aug. 2017) (Year: 2017).*
(Continued)

*Primary Examiner* — Yevgeny Valenrod
*Assistant Examiner* — Blaine G Doletski
(74) *Attorney, Agent, or Firm* — Birch, Stewart, Kolasch & Birch, LLP

(57) ABSTRACT

Provided is an acetic acid production method that enables smooth reduction and/or increase of acetic acid production with easy operation and can industrially efficiently, stably produce acetic acid with maintained quality even when the acetic acid production volume is changed. The acetic acid production method includes a carbonylation step in which methanol is reacted with carbon monoxide in a continuous system in the presence of a catalytic system, acetic acid, methyl acetate, and water, where the catalytic system includes a metal catalyst and methyl iodide. The carbonylation step employs two or more reactors disposed in parallel.

6 Claims, 4 Drawing Sheets

(51) Int. Cl.
　　*B01J 31/20*　　(2006.01)
　　*C07C 51/44*　　(2006.01)
(52) U.S. Cl.
　　CPC ............... *B01J 2219/00038* (2013.01); *B01J 2531/822* (2013.01); *B01J 2531/827* (2013.01)
(58) Field of Classification Search
　　CPC ........ B01J 2219/00038; B01J 2531/827; B01J 2531/822; B01J 2231/34
　　See application file for complete search history.

(56) References Cited

U.S. PATENT DOCUMENTS

| | | |
|---|---|---|
| 2013/0172601 A1 | 7/2013 | Zhu et al. |
| 2013/0184491 A1* | 7/2013 | Le Berre ............... C07C 51/12 562/519 |
| 2015/0299084 A1 | 10/2015 | Shimizu et al. |
| 2016/0137576 A1* | 5/2016 | Liu ........................ C07C 51/12 562/519 |
| 2019/0127299 A1 | 5/2019 | Takahashi et al. |

FOREIGN PATENT DOCUMENTS

| | | | |
|---|---|---|---|
| EP | 3333147 A1 * | 6/2018 | ............ C07C 51/44 |
| IN | 201817007368 A | 6/2018 | |
| JP | 7-25813 A | 1/1995 | |
| JP | 2014-162746 A | 9/2014 | |
| JP | 2015-166315 A | 9/2015 | |
| WO | WO 2006/122563 A1 | 11/2006 | |
| WO | WO 2014/097867 A1 | 6/2014 | |
| WO | WO 2017/183702 A1 | 10/2017 | |
| WO | WO 2018/078924 A1 | 5/2018 | |

OTHER PUBLICATIONS

International Search Report (PCT/ISA/210) issued in PCT/JP2018/025077, dated Aug. 7, 2018.
Written Opinion (PCT/ISA/237) issued in PCT/JP2018/025077, dated Aug. 7, 2018.
Extended European Search Report dated Jun. 16, 2020, in European Patent Application No. 18905889.4.
English translation of Written Opinion dated Oct. 29, 2019, in PCT/JP2018/0250777 (Forms PCT/IB/310, EPO Form 1210, and PCT/ISA/237).
Office Action dated May 4, 2022, in Indian Patent Application No. 202117003066.

* cited by examiner

[Fig. 1]
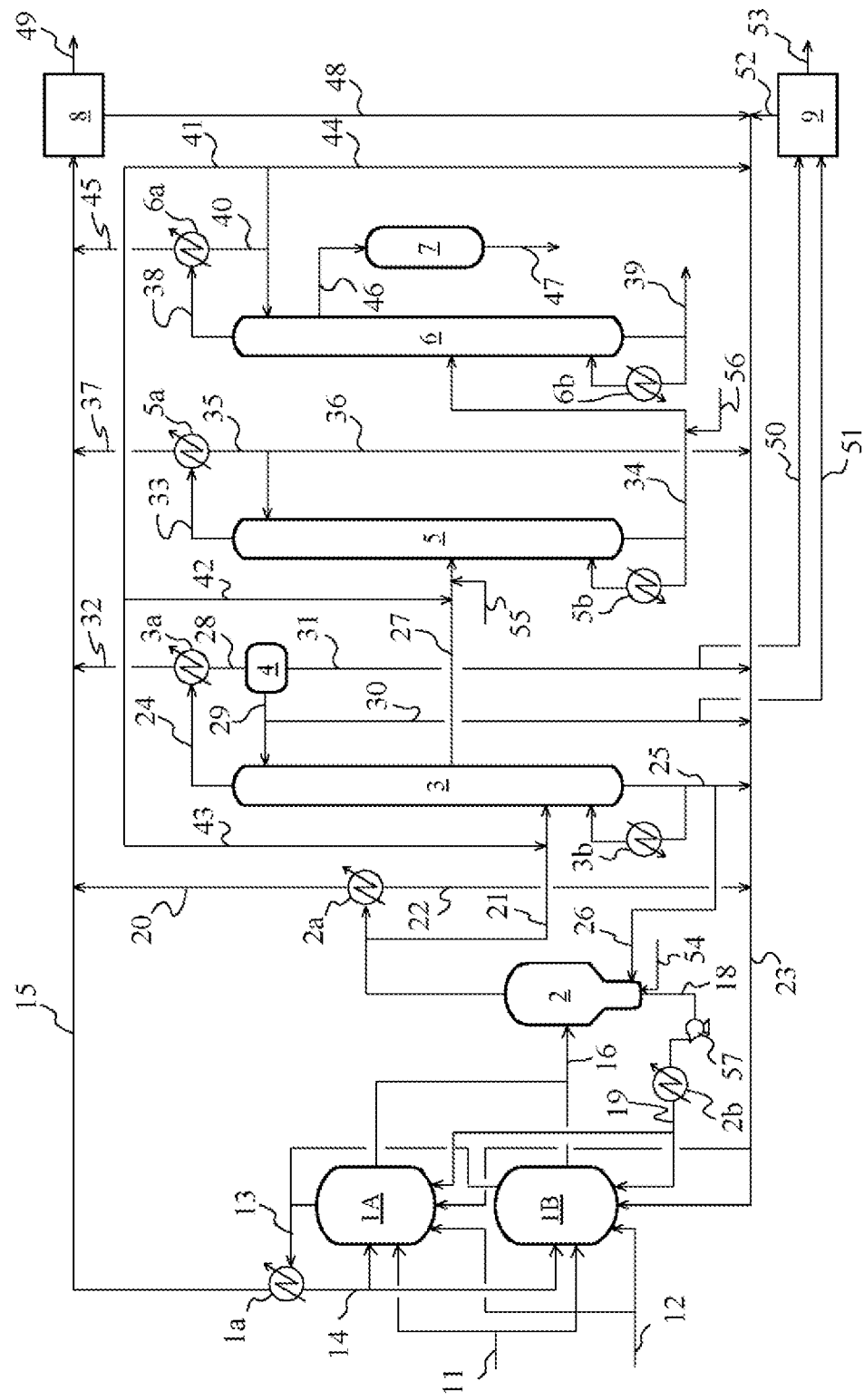

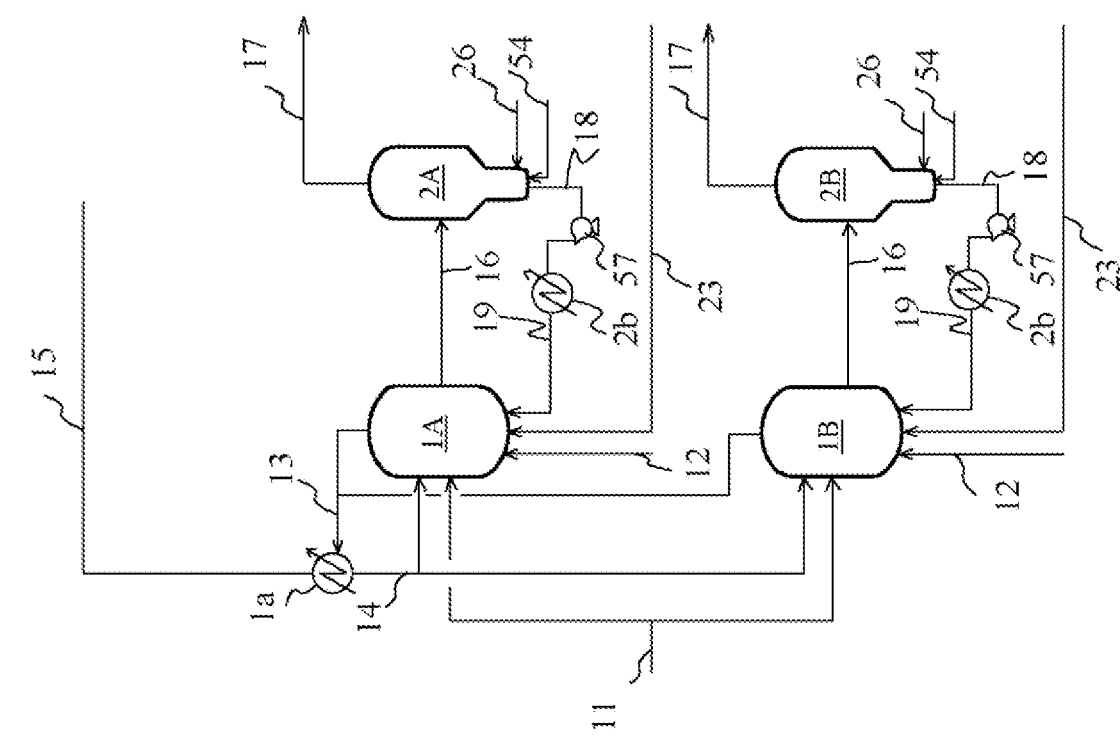
[Fig.2]

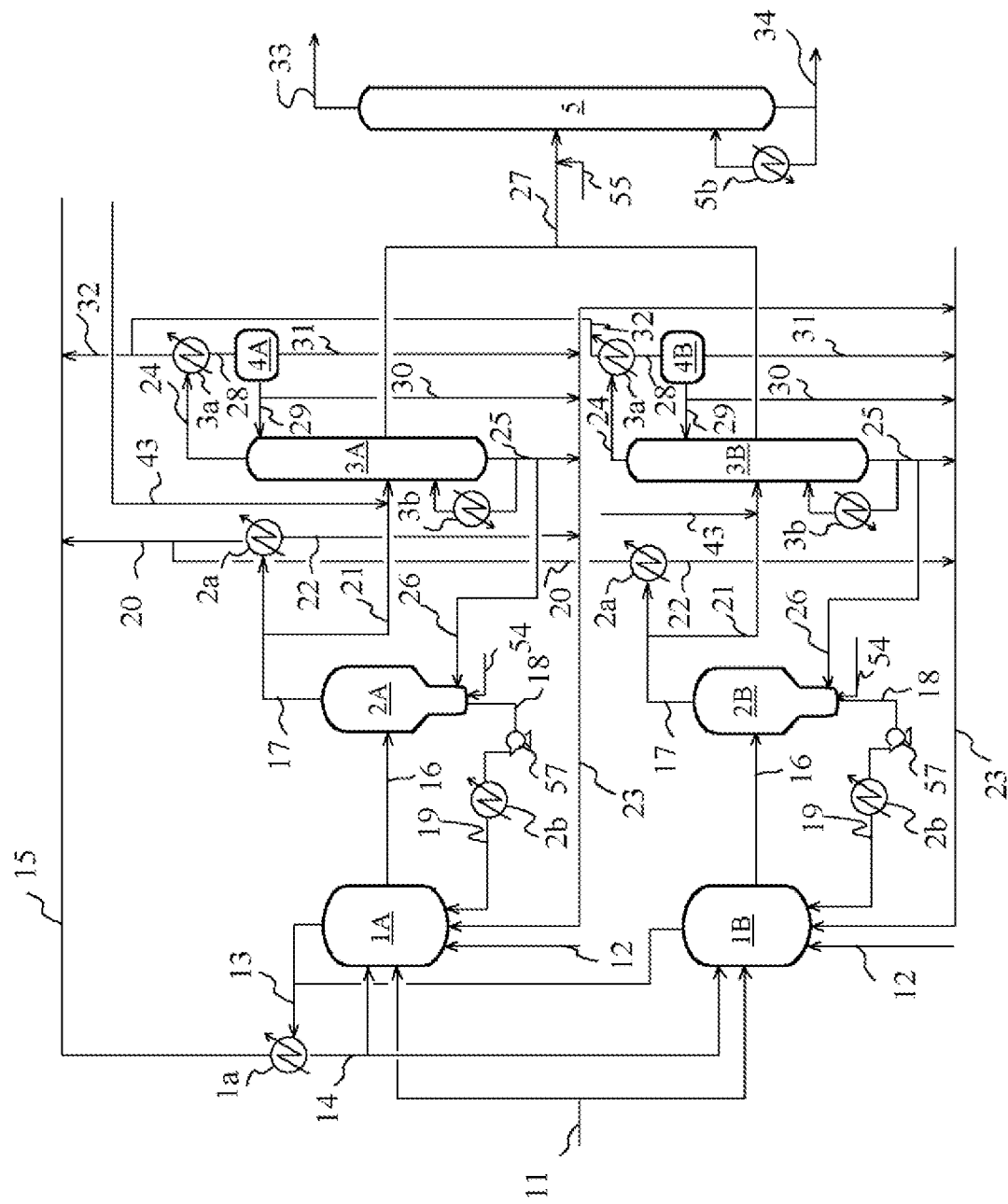
[Fig.3]

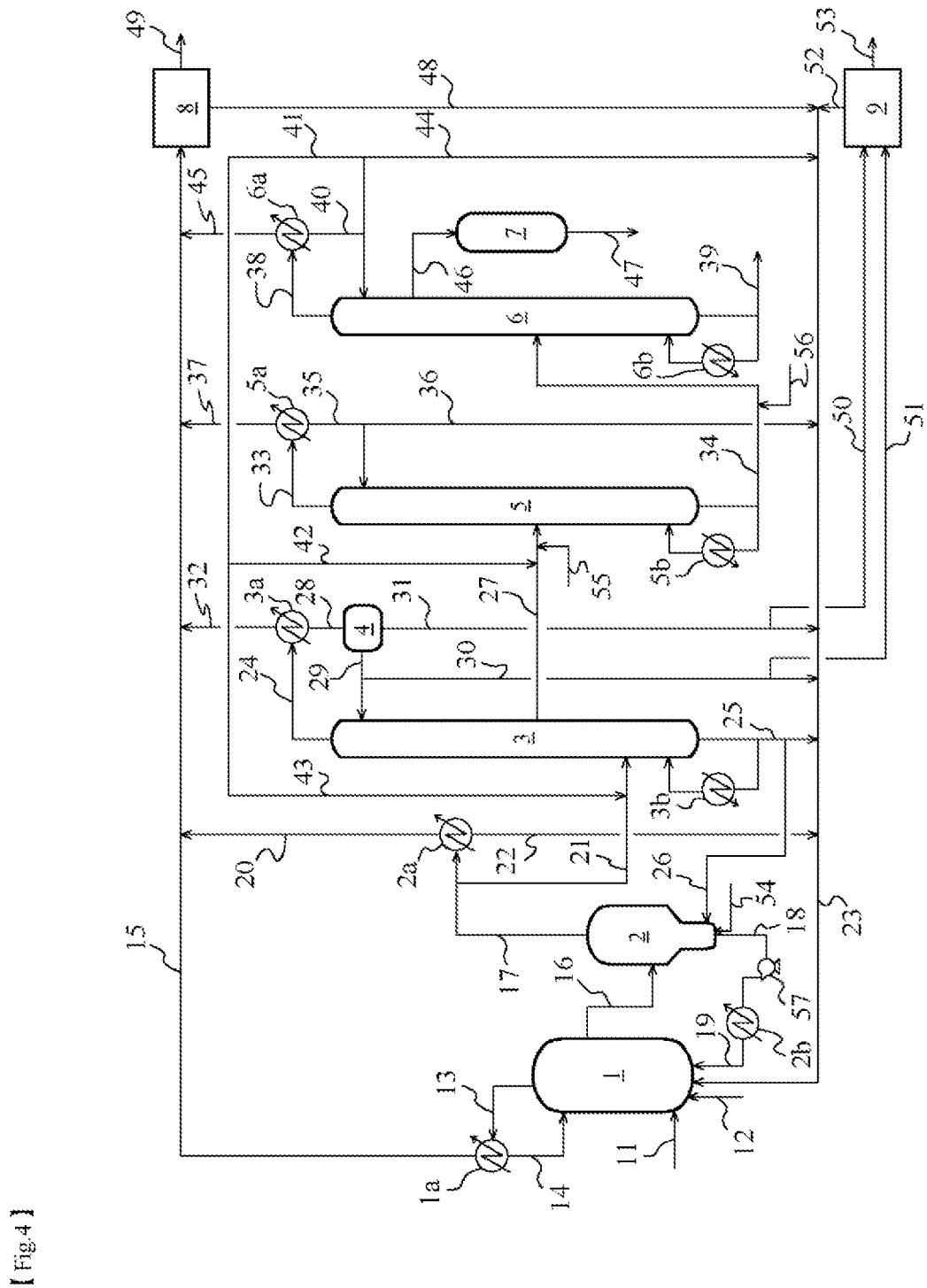
[Fig.4]

METHOD FOR PRODUCING ACETIC ACID

TECHNICAL FIELD

The present invention relates to methods for producing acetic acid.

BACKGROUND ART

In general in a methanol-acetic acid process, there are introduced, into a reactor, starting material methanol, starting material carbon monoxide, a catalyst solution (acetic acid solution including a metal catalyst) recycled from the bottom of an evaporator, and methyl iodide as a promoter recycled from a purification system. In the reactor, the starting material methanol is reacted with carbon monoxide to form acetic acid (e.g., Patent Literature (PTL) 1).

In plant designing, the capacities of the reactor, the evaporator, and a methyl iodide reservoir (such as a decanter) are designed larger than scales corresponding to the planned acetic acid production volume not so larger, but only by about one tenth, so as to optimize the installation cost.

Assume that the acetic acid production volume is to be changed (e.g., production is to be reduced or increased) in a conventional plant according to a continuous process. In this case, the production volume is generally changed by changing the amounts of the starting material methanol and the starting material carbon monoxide to be fed, and regulating the reaction rate, to change the acetic acid production volume per unit time. For example, when the acetic acid production volume is to be reduced (reduction of production), the reaction rate is lowered to lower the acetic acid formation rate, by lowering the concentrations of the catalyst and the promoter in the reactor, and/or by lowering the reaction temperature.

However, the capacity of the evaporator, for example, is designed according to the originally planned production volume, as described above. Accordingly, the catalyst concentration in the reactor, when intended to be lowered, can be lowered at most by about one tenth, even by reducing the amount of acetic acid evaporation and thereby increasing the liquid volume in the evaporator in order to recycle a solution containing the metal catalyst in a lower concentration.

Also assume that the reaction rate is intended to be changed by changing the reaction temperature. In this case, however, acetic acid fails to be evaporated in a desired amount in the evaporator at an excessively low reaction temperature; whereas the catalyst is entrained in a larger amount in the evaporator at an excessively high reaction temperature, and this leads to catalyst loss.

CITATION LIST

Patent Literature

PTL 1: Japanese Unexamined Patent Application Publication (JP-A) No. H07-25813

SUMMARY OF INVENTION

Technical Problem

Such conventional acetic acid production methods fail to significantly change the catalyst concentration and/or the promoter concentration and fail to significantly change the reaction temperature in the reactor, as described above, and thereby fail to smoothly reduce and/or increase acetic acid production.

Accordingly, the present invention has an object to provide a method that enables smooth reduction and/or increase of acetic acid production with easy operation, and enables industrially efficient, stable production of acetic acid with maintained quality even when the acetic acid production volume is changed.

Solution to Problem

After intensive investigations to achieve the object, the inventor of the present invention found that an acetic acid production method, when including a carbonylation step using two or more parallel reactors, enables smooth reduction and increase of acetic acid production with easy operation and enables industrially efficient, stable production of acetic acid with maintained quality even when the acetic acid production volume is changed, where the carbonylation step is the step or reacting methanol with carbon monoxide in a continuous system in the presence of a catalytic system, acetic acid, methyl acetate, and water, and where the catalytic system includes a metal catalyst and methyl iodide. The present invention has been made on the basis of these findings.

Specifically, the present invention provides, in one aspect, an acetic acid production method that includes a carbonylation step (reaction step). In the carbonylation step, methanol is reacted with carbon monoxide in a continuous system in the presence of a catalytic system, acetic acid, methyl acetate, and water, where the catalytic system includes a metal catalyst and methyl iodide. The carbonylation step employs two or more reactors disposed in parallel. This acetic acid production method is hereinafter also referred to as a "first acetic acid production method".

The first acetic acid production method may further include, in addition to the carbonylation step, an evaporation step. In the evaporation step, a reaction mixture from the carbonylation step is separated, using an evaporator, into a vapor stream and a residue stream. The evaporator includes two or more evaporators disposed in parallel and coupled respectively to the two or more parallel reactors.

The first acetic acid production method may further include, in addition to the carbonylation step, an evaporation step and a light ends-removing step.

In the evaporation step, a reaction mixture from the carbonylation step is separated, using an evaporator, into a vapor stream and a residue stream.

In the light ends-removing step, the vapor stream is separated, by distillation using a distillation column, into an overhead stream rich in at least one light end selected from methyl iodide and acetaldehyde, and an acetic acid stream rich in acetic acid, and the overhead stream is subjected sequentially to condensation and to liquid-liquid separation using two or more decanters, to give an aqueous phase and an organic phase.

In the method, the evaporator may include two or more evaporators disposed in parallel and coupled respectively to the parallel reactors, and the distillation column may include two or more distillation columns disposed in parallel and coupled respectively to the parallel evaporators.

In the first acetic acid production method, the acetic acid production volume may be reduced and/or increased by reducing and/or increasing the number of reactors in operation, of the two or more parallel reactors.

In a preferred embodiment of the first acetic acid production method, during operation with increase or decrease in number of reactors in operation, the reactor(s) in operation is operated at a reaction temperature of 170° C. or higher, and at least one of conditions (i) to (vii) is met regardless of the number of reactors in operation, where the conditions (i) to (vii) are expressed as follows:

(i) variations in metal catalyst concentration and methyl iodide concentration in the reactor(s) in operation are each within ±50%;

(ii) the catalytic system further includes an iodide salt, and a variation in iodide salt concentration in the reactor(s) in operation falls within ±50%;

(iii) a variation in reaction temperature in the reactor(s) in operation falls within ±20° C.;

(iv) a variation in at least one of acetic acid concentration, methyl acetate concentration, and water concentration in the reactor(s) in operation falls within ±50%;

(v) a variation in hydrogen partial pressure in the reactor(s) in operation falls within ±50%;

(vi) a variation in reaction rate in the reactor(s) in operation falls within ±50%; and (vii) a variation in acetic acid space time yield in the reactor(s) in operation falls within ±40%.

In the first acetic acid production method, at least one of the conditions (i) to (vii) is preferably met between before and after switchover to increase or decrease in number of reactors in operation.

In a preferred embodiment, the first acetic acid production method further includes, in addition to the carbonylation step, an evaporation step.

In the evaporation step, a reaction mixture from the carbonylation step is separated, using an evaporator, into a vapor stream and a residue stream.

In the evaporation step, a liquid volume in the evaporator is 1 to 100 parts by volume per 100 parts by volume of the total liquid volume in the parallel reactors, where, when the evaporator includes two or more evaporators disposed in parallel, the term "liquid volume in the evaporator" is read as "total liquid volume in the two or more evaporators".

In a preferred embodiment, the first acetic acid production method further includes, in addition to the carbonylation step, an evaporation step and a light ends-removing step.

In the evaporation step, a reaction mixture from the carbonylation step is separated, using an evaporator, into a vapor stream and a residue stream.

In the light ends-removing step, the vapor stream is separated, by distillation using a distillation column, into an overhead stream rich in at least one light end selected from methyl iodide and acetaldehyde, and an acetic acid stream rich in acetic acid, and the overhead stream is subjected sequentially to condensation and to liquid-liquid separation using a decanter, to give an aqueous phase and an organic phase.

In the light ends-removing step, a liquid volume in the decanter is 1 to 100 parts by volume per 100 parts by volume of the total liquid volume in the parallel reactors, where, when the decanter includes two or more decanters disposed in parallel, the term "liquid volume in the decanter" is read as "total liquid volume in the two or more decanters".

In a preferred embodiment, the first acetic acid production method further includes, in addition to the carbonylation step, an evaporation step and a light ends-removing step.

In the evaporation step, a reaction mixture from the carbonylation step is separated, using an evaporator or evaporators, into a vapor stream and a residue stream.

In the light ends-removing step, the vapor stream is separated, by distillation, into an overhead stream rich in at least one light end selected from methyl iodide and acetaldehyde, and an acetic acid stream rich in acetic acid, and the overhead stream is subjected sequentially to condensation and to liquid-liquid separation using a decanter or decanters, to give an aqueous phase and an organic phase.

During operation with increase or decrease in number of reactors in operation, the reactor(s) in operation is operated at a reaction temperature of 170° C. or higher, and at least one of conditions (viii) to (x) is met regardless of the number of reactors in operation, where the conditions (viii) to (x) are expressed as follows:

(viii) a variation in liquid level in the reactor(s) in operation falls within ±20%;

(ix) a variation in liquid level in the working evaporator(s) falls within ±20%; and (x) a variation in liquid level in the working decanter(s) falls within ±20%.

The present invention also provides, in another aspect, an acetic acid production method that includes a carbonylation step.

In the carbonylation step, methanol is reacted with carbon monoxide in a continuous system in the presence of a catalytic system, acetic acid, methyl acetate, and water, where the catalytic system includes a metal catalyst and methyl iodide.

In the carbonylation step, a variation in acetic acid space time yield is held within ±40% upon reduction of the acetic acid production volume down to 30% to 90%. This acetic acid production method is hereinafter also referred to as a "second acetic acid production method".

In a preferred embodiment of the second acetic acid production method, two or more reactors are used in parallel, and the number of reactors in operation is reduced to reduce the acetic acid production volume.

Advantageous Effects of Invention

The present invention employs two or more reactors disposed in parallel, thereby enables smooth reduction and/or increase of acetic acid production with easy operation, and, even when the acetic acid production volume is changed, less undergoes changes in amount of formed impurities and enables industrially efficient, stable acetic acid production with maintained quality.

BRIEF DESCRIPTION OF DRAWINGS

FIG. 1 depicts an acetic acid production flow chart illustrating an embodiment of the present invention;

FIG. 2 depicts a schematic flow chart illustrating an embodiment in which two reactors disposed or coupled in parallel are coupled respectively to two evaporators disposed in parallel;

FIG. 3 depicts a schematic flow chart illustrating an embodiment in which two reactors disposed or coupled in parallel are coupled respectively to two evaporators disposed in parallel, and the two evaporators are coupled respectively to two distillation columns disposed in parallel; and FIG. 4 depicts an exemplary conventional acetic acid production flow chart.

DESCRIPTION OF EMBODIMENTS

The present invention will be illustrated in further detail below, with reference to the attached drawings as needed. It should be noted, however, that embodiments illustrated below are never construed to limit the scope of the present invention.

FIG. 1 depicts an exemplary acetic acid production flow chart (methanol carbonylation process in which the reaction is performed in a continuous system) according to an embodiment of the present invention. Acetic acid production equipment according to this acetic acid production flow includes reactors 1A and 1B, an evaporator 2, a distillation column 3, a decanter 4, a distillation column 5, a distillation column 6, an ion exchange resin column 7, a scrubbing system 8, an acetaldehyde-removing system 9, condensers 1a, 2a, 3a, 5a, and 6a, a heat exchanger 2b, reboilers 3b, 5b, and 6b, lines 11 to 56, and a pump 57. The equipment is configured so as to be capable of continuously producing acetic acid. In an acetic acid production method according to the embodiment, a reaction step, an evaporation step (flash step), a first distillation step, a second distillation step, a third distillation step, and an adsorptive removing step are performed respectively in the reactors 1A and 1B, the evaporator 2, the distillation column 3, the distillation column 5, the distillation column 6, and the ion exchange resin column 7. The first distillation step, the second distillation step, and the third distillation step are also respectively referred to as a light ends-removing step, a dehydration step, and a heavy ends-removing step. Steps to be employed in the present invention are not limited to those mentioned above. For example, the equipment may not include one or more facilities such as the distillation column 6, the ion exchange resin column 7, and the acetaldehyde-removing system 9 (such as an acetaldehyde-removing column). The equipment may further include a product column downstream from the ion exchange resin column 7, as described later.

The first acetic acid production method is an acetic acid production method that includes a carbonylation step. In the carbonylation step, methanol is reacted with carbon monoxide in a continuous system in the presence of a catalytic system, acetic acid, methyl acetate, and water, where the catalytic system includes a metal catalyst and methyl iodide. The carbonylation step employs two or more reactors disposed in parallel. This configuration allows the acetic acid production volume to be increased or decreased by increasing or decreasing the number of reactors in operation, when the acetic acid production volume is demanded to be changed (e.g., when the production is reduced or increased). As used herein, the term "to operate" refers to "to work" or "to put something in operation".

Assume that the reactors 1A and 1B are used in parallel as illustrated in FIG. 1 and that the acetic acid production volume is to be reduced to half the regular production volume. In this case, the acetic acid production volume may be reduced typically by reducing the amounts of the starting material methanol and the starting material carbon monoxide individually to half in the entire process, and operating only one of the reactors 1A and 1B (half load). The switchover to one-reactor operation as above enables efficient operation, because the reaction mixture has a composition that is approximately the same as in the two-reactor operation (full load). However, if two or more reactors, even when used, are coupled in series, the advantageous effects of the present invention are not obtained, because the configuration hardly increases and decreases the number of reactors in operation according to the demanded acetic acid production volume. The carbonylation reaction in the present invention has to be a step according to a continuous system. This is because an operation according to a batch system or semi-batch system is capable of flexibly changing the amounts of the starting materials and the catalytic system as occasion demands and has not to dare to employ two or more parallel reactors.

The reactors 1A and 1B are units with which the reaction step is performed. This reaction step is the step of continuously forming acetic acid through a reaction (methanol-carbonylation reaction) represented by Chemical Formula (1) below. During steady operation of the acetic acid production equipment, the reactors 1A and 1B contain or house a reaction mixture, which is stirred typically with a stirrer. The reaction mixture includes starting materials methanol and carbon monoxide, a metal catalyst, a promoter, water, production target acetic acid, and various by-products. In the reaction mixture, a liquid phase and a gas phase are in an equilibrium state. Chemical Formula (1) is expressed as follows:

$$CH_3OH + CO \rightarrow CH_3COOH \tag{1}$$

The starting materials in the reaction mixture are liquid methanol and gaseous carbon monoxide. Methanol is fed from a methanol storage unit (not shown) through the line 11 to the reactors 1A and 1B continuously at a predetermined flow rate.

Carbon monoxide is fed from a carbon monoxide storage unit (not shown) through the line 12 to the reactors 1A and 1B continuously at a predetermined flow rate. The carbon monoxide does not always have to be pure carbon monoxide and may include a small amount (typically 5 mass percent or less, and preferably 1 mass percent or less) of one or more other gases such as nitrogen, hydrogen, carbon dioxide, and oxygen.

The metal catalyst in the reaction mixture is used to promote or accelerate the methanol-carbonylation reaction and may be selected typically from rhodium catalysts and iridium catalysts. A non-limiting example of the rhodium catalysts is a rhodium complex represented by the chemical formula: $[Rh(CO)_2I_2]^-$. A non-limiting example of the iridium catalysts is an iridium complex represented by the chemical formula: $[Ir(CO)_2I_2]^-$. The metal catalyst is preferably selected from metal complex catalysts. The catalyst may be present in the reaction mixture in a concentration (in terms of metal) of typically 100 to 10000 ppm by mass, preferably 200 to 5000 ppm by mass, and furthermore preferably 400 to 2000 ppm by mass, relative to the totality of the liquid phase of the reaction mixture.

The promoter is an iodide to assist the action of the catalyst and may be selected typically from methyl iodide and ionic iodides. Methyl iodide can offer the action of promoting catalysis of the catalyst. Methyl iodide may be present in a concentration of typically 1 to 20 mass percent, relative to the totality of the liquid phase of the reaction mixture. The ionic iodides are iodides that form iodide ions in a liquid reaction mixture, of which ionic metal iodides are typified. The ionic iodides can offer the action of stabilizing the catalyst, and/or the action of restraining side reactions. Non-limiting examples of the ionic iodides include alkali metal iodides such as lithium iodide, sodium iodide, and potassium iodide. The ionic iodide(s) may be present in the reaction mixture in a concentration of typically 1 to 25 mass percent, and preferably 5 to 20 mass percent, relative to the totality of the liquid phase of the reaction mixture. For example, when an iridium catalyst is used, a ruthenium compound and/or an osmium compound may be used as the promoter. These compounds may be used in a total amount of typically 0.1 to 30 moles (in terms of metal), and preferably 0.5 to 15 moles (in terms of metal), per mole (in terms of metal) of iridium.

Water in the reaction mixture is a component necessary for the formation of acetic acid, due to the reaction mechanism of the methanol-carbonylation reaction, and is a component necessary for dissolving water-soluble components in the reaction system. The water may be present in the reaction mixture in a concentration of typically 0.1 to 15 mass percent, preferably 0.8 to 10 mass percent, furthermore preferably 1 to 6 mass percent, and particularly preferably 1.5 to 4 mass percent, relative to the totality of the liquid phase of the reaction mixture. The water concentration is preferably 15 mass percent or less, so as to minimize energy necessary for removing water in the acetic acid purification process and for performing the acetic acid production more efficiently. To control the water concentration, water may be fed to the reactors 1A and 1B continuously at a predetermined flow rate.

Acetic acid in the reaction mixture includes acetic acid that has been charged into the reactors 1A and 1B before operation of the acetic acid production equipment; and acetic acid that is formed as a main product of the methanol-carbonylation reaction. Acetic acid as above can function as a solvent in the reaction system. Acetic acid may be present in the reaction mixture in a concentration of typically 50 to 90 mass percent, and preferably 60 to 80 mass percent, relative to the totality of the liquid phase of the reaction mixture.

A non-limiting example of major by-products contained in the reaction mixture is methyl acetate. Methyl acetate can be formed through reaction between acetic acid and methanol. Methyl acetate may be present in the reaction mixture in a concentration of typically 0.1 to 30 mass percent, and preferably 1 to 10 mass percent, relative to the totality of the liquid phase of the reaction mixture. Another non-limiting example of the by-products contained in the reaction mixture is hydrogen iodide. When the catalyst with or without the promoter as above is used, hydrogen iodide is unavoidably formed due to the reaction mechanism of the methanol-carbonylation reaction. Hydrogen iodide may be present in the reaction mixture in a concentration of typically 0.01 to 2 mass percent, relative to the totality of the liquid phase of the reaction mixture.

Non-limiting examples of the by-products also include hydrogen, methane, carbon dioxide, acetaldehyde, crotonaldehyde, 2-ethylcrotonaldehyde, butyl acetate, dimethyl ether, alkanes, formic acid, and propionic acid; as well as alkyl iodides such as ethyl iodide, propyl iodide, butyl iodide, hexyl iodide, and decyl iodide.

The reaction mixture may also include metals exemplified by corrosion metals (also called corrosible metals) such as iron, nickel, chromium, manganese, and molybdenum, where the corrosion metals are metals resulting from corrosion of the equipment; and other metals such as cobalt, zinc, and copper. Hereinafter, the corrosion metals and other metals are also generically referred to as "metals such as corrosion metals".

In the reactors 1A and 1B housing the reaction mixture as above, the reaction temperature is typically 170° C. or higher (e.g., 171° C. or higher), preferably 175° C. or higher (e.g., 176° C.), more preferably 180° C. or higher (e.g., 181° C. or higher), furthermore preferably 182° C. or higher (e.g., 183° C. or higher), particularly preferably 184° C. or higher (e.g., 185° C. or higher), and especially preferably 186° C. or higher (e.g., 187° C. or higher). The operation of the reactors at a reaction temperature of 170° C. or higher allows acetic acid to evaporate sufficiently in the subsequent (downstream) flash step. An operation performed at an excessively high reaction temperature (e.g., at a temperature higher than 250° C.) may increase the entrainment of the vapor stream to the distillation column, and this disadvantageously leads to loss of the catalyst and the promoter.

The reaction pressure in terms of total pressure is set typically to 1.5 to 5 MPa (e.g., 2.0 to 3.5 MPa) (absolute pressure); and the carbon monoxide partial pressure is set to typically 0.2 to 2.5 MPa (e.g., 0.4 to 1.8 MPa) (absolute pressure), preferably 0.6 to 1.6 MPa (absolute pressure), and furthermore preferably 0.9 to 1.4 MPa (absolute pressure).

During operation of the equipment, vapors in the gas phase in the reactors 1A and 1B typically include carbon monoxide, hydrogen, methane, carbon dioxide, nitrogen, oxygen, methyl iodide, hydrogen iodide, water, methyl acetate, acetic acid, dimethyl ether, methanol, acetaldehyde, formic acid, and propionic acid. Hydrogen is contained in carbon monoxide used as the starting material, and, in addition, is formed by a shift reaction ($CO+H_2O \rightarrow H_2+CO_2$) which occurs in the reactors 1A and 1B. The hydrogen partial pressure in the reactors 1A and 1B is typically 0.001 MPa (absolute pressure) or more (e.g., 0.005 MPa or more), preferably 0.01 MPa (absolute pressure) or more (e.g., 0.015 MPa or more), more preferably 0.02 MPa (absolute pressure) or more, furthermore preferably 0.04 MPa (absolute pressure) or more, and particularly preferably 0.06 MPa (absolute pressure) or more (e.g., 0.07 MPa (absolute pressure) or more). The upper limit of the hydrogen partial pressure in the reactors is typically 0.5 MPa (absolute pressure) (in particular, 0.2 MPa (absolute pressure)). An excessively high hydrogen partial pressure in the reactors may invite increase in amount of acetaldehyde formation and thereby cause increase in amount of crotonaldehyde formation by aldol condensation. In contrast, an excessively low hydrogen partial pressure may significantly impede the reaction: crotonaldehyde→butyl alcohol, whereas a minute variation in hydrogen partial pressure may cause the reaction rate to vary significantly, and this may cause the operation to be unstable. The vapors in the gas phase in the reactors 1A and 1B can be drawn from the reactors 1A and 1B through the line 13. The inside pressure of the reactors 1A and 1B can be controlled by regulating the amount of the vapors to be drawn. For example, the pressure in the reactors 1A and 1B is held constant. The vapors drawn from the reactors 1A and 1B are introduced into the condenser 1a.

During operation with increase or decrease in number of reactors in operation in the acetic acid production method according to the present invention, it is accepted that the reactor(s) in operation (working reactor(s)) is operated at a reaction temperature of 170° C. or higher, and at least one of conditions (i) to (vii) is met regardless of the number of reactors in operation, where the conditions (i) to (vii) are expressed as follows:

(i) variations in metal catalyst concentration and methyl iodide concentration in the reactor(s) in operation fall within ±50%;

(ii) the catalytic system further includes an iodide salt, and a variation in iodide salt concentration in the reactor(s) in operation falls within ±50%;

(iii) a variation in reaction temperature in the reactor(s) in operation falls within ±20° C.;

(iv) a variation in at least one of acetic acid concentration, methyl acetate concentration, and water concentration in the reactor(s) in operation falls within ±50%;

(v) a variation in hydrogen partial pressure in the reactor(s) in operation falls within ±50%;

(vi) a variation in reaction rate in the reactor(s) in operation falls within ±50%; and (vii) a variation in acetic acid space time yield in the reactor(s) in operation falls within ±40%.

The variation or variations are observed typically for 5 days, 10 days, 30 days, half a year, or one year.

At least one of the conditions (i) to (vii) may be met between before and after switchover to increase or decrease in number of reactors in operation.

As used herein, the term "variation" between before and after switchover to increase or decrease in number of reactors in operation refers to a variation of the average of parameter values over a predetermined period (e.g., 5 days, 10 days, 30 days, half a year, or one year) after switchover to increase or decrease, relative to the average of parameter values over a predetermined period (e.g., 5 days, 10 days, 30 days, half a year, or one year) before switchover to increase or decrease.

Relating to the condition (i), the variation in metal catalyst concentration in the reactor(s) in operation falls typically within ±50%, preferably within ±40%, more preferably within ±30%, furthermore preferably within ±20%, particularly preferably within ±10%, and especially preferably within +5%. The lower limit of the variation in metal catalyst concentration is ±0%, but the variation is generally ±0.001% or more. The variation in methyl iodide concentration in the reactor(s) in operation is typically within ±50%, preferably within ±40%, more preferably within ±30%, furthermore preferably within ±20%, particularly preferably within ±10%, and especially preferably within ±5%. The lower limit of the variation in methyl iodide concentration is ±0%, but the variation is generally ±0.001% or more. The control of the variations in metal catalyst concentration and methyl iodide concentration in the reactor(s) in operation within ±50%, regardless of the number of reactors in operation, contributes to maintenance of the industrially efficient reaction rate.

For example, in the embodiment illustrated in FIG. 1, a non-limiting example of the switchover to increase or decrease in number of reactors in operation is the case where only the reactor 1A alone is operated after both the reactors 1A and 1B are operated. Assume that the variation in metal catalyst concentration in the reactor(s) in operation falls within ±50% between before and after switchover to increase or decrease in number of reactors in operation. This means that the variation in metal catalyst concentration in the reactor 1A after switchover of number of reactors in operation falls within ±50% relative to the metal catalyst concentration in the reactor 1A and the metal catalyst concentration in the reactor 1B before switchover of number of reactors in operation. Before switchover of number of reactors in operation, the metal catalyst concentration in the reactor 1A is approximately equal to the metal catalyst concentration in the reactor 1B. This is probably also true for the variation in methyl iodide concentration in the reactor(s) in operation between before and after switchover to increase or decrease in number of reactors in operation.

Relating to the condition (ii), when the catalytic system further includes an iodide salt, the variation in iodide salt concentration in the reactor(s) in operation is typically within ±50%, preferably within ±40%, more preferably within ±30%, furthermore preferably within ±20%, particularly preferably within ±10%, and especially preferably within ±5%. The lower limit of the variation in iodide salt concentration is ±0%, but the variation is generally ±0.001% or more. Control of the variation in iodide salt concentration in the reactor(s) in operation within ±50%, regardless of the number of reactors in operation, contributes to maintenance of industrially efficient reaction rate. Assume that the variation in iodide salt concentration in the reactor(s) in operation between before and after switchover to increase or decrease in number of reactors in operation falls within ±50%. The meaning of this is similar to that in the variation in metal catalyst concentration.

Relating to the condition (iii), the variation in reaction temperature in the reactor(s) in operation is typically within ±20° C., preferably within ±15° C., more preferably within ±10° C., furthermore preferably within ±8° C., particularly preferably within ±5° C., and especially preferably within ±3° C. The lower limit of the variation in reaction temperature is ±0° C., but the variation is generally ±0.001° C. or higher. Control of the variation in reaction temperature in the reactor(s) in operation within ±20° C., regardless of the number of reactors in operation, contributes to maintenance of industrially efficient reaction rate. Assume that the variation in reaction temperature in the reactor(s) in operation between before and after switchover to increase or decrease in number of reactors in operation falls within ±20° C. The meaning of this is similar to that in the variation in metal catalyst concentration.

Relating to the condition (iv), the variation in acetic acid concentration in the reactor(s) in operation is typically within ±50%, preferably within ±40%, more preferably within ±30%, furthermore preferably within ±20%, particularly preferably within ±10%, and especially preferably within ±5%. The lower limit of the variation in acetic acid concentration is ±0%, but the variation is generally ±0.001% or more. The variation in methyl acetate concentration in the reactor(s) in operation is typically within ±50%, preferably within ±40%, more preferably within ±30%, furthermore preferably within ±20%, particularly preferably within ±10%, and especially preferably within ±5%. The lower limit of the variation in methyl acetate concentration is ±0%, but the variation is generally ±0.001% or more. The variation in water concentration in the reactor(s) in operation is typically within ±50%, preferably within ±40%, more preferably within ±30%, furthermore preferably within ±20%, particularly preferably within ±10%, and especially preferably within ±5%. The lower limit of the variation in water concentration is ±0%, but the variation is generally ±0.001% or more. Control of the variations in acetic acid concentration, methyl acetate concentration, and water concentration in the reactor(s) in operation within ±50%, regardless of the number of reactors in operation, contributes to maintenance of industrially efficient reaction rate. Assume that the variations in acetic acid concentration, methyl acetate concentration, and water concentration in the reactor(s) in operation between before and after switchover to increase or decrease in number of reactors in operation fall within ±50%. The meaning of this is similar to that in the variation in the metal catalyst concentration.

Relating to the condition (v), the variation in hydrogen partial pressure in the reactor(s) in operation is typically within ±50%, preferably within ±40%, more preferably within ±30%, furthermore preferably within ±20%, particularly preferably within ±10%, and especially preferably within +5%. The lower limit of the variation in hydrogen partial pressure is ±0%, but the variation is generally ±0.001% or more. Control of the variation in hydrogen partial pressure in the reactor(s) in operation within ±50%, regardless of the number of reactors in operation, contributes to maintenance of industrially efficient reaction rate. In general, an excessively high hydrogen partial pressure in a reactor may cause increase in amount of acetaldehyde formation and thereby cause increase in amount of crotonaldehyde formation by aldol condensation. In contrast, an excessively low hydrogen partial pressure may significantly impede the reaction: crotonaldehyde→butyl alcohol, whereas a minute variation in hydrogen partial pressure may cause the reaction rate to vary significantly, and this may cause the operation to be unstable. Advantageously, the acetic acid production method according to the present invention contributes to stable operation, because the method controls or restrains the variation in hydrogen partial pressure within the specific range. Assume that the variation in hydrogen partial pressure in the reactor(s) in operation falls within ±50% between before and after switchover to increase or decrease in number of reactors in operation. The meaning of this is similar to that in the variation in the metal catalyst concentration.

Relating to the condition (vi), the variation in reaction rate in the reactor(s) in operation is typically within ±50%, preferably within ±40%, more preferably within ±30%, furthermore preferably within ±20%, particularly preferably within ±10%, and especially preferably within ±5%. The lower limit of the variation in reaction rate is ±0%, but the variation is generally ±0.001% or more. In general, the reaction rate can be adjusted by appropriately selecting or determining one or more parameters such as reaction temperature, catalyst concentrations (such as metal catalyst concentration and methyl iodide concentration), carbon monoxide concentration (or carbon monoxide partial pressure), hydrogen partial pressure, methyl acetate, and water. With the present invention, advantageously, these parameters are kept within specific ranges and are restrained from varying significantly, regardless of the number of reactors in operation. Assume that the variation in reaction rate in the reactor(s) in operation falls within ±50% between before and after switchover to increase or decrease in number of reactors in operation. The meaning of this is similar to that in the variation in the metal catalyst concentration.

Relating to the condition (vii), the variation in acetic acid space time yield (also called "acetic acid formation rate") in the reactor(s) in operation is typically within ±40%, within ±35%, within ±30%, within ±25%, within 20%, preferably within ±15%, more preferably within ±10%, furthermore preferably within ±8%, particularly preferably within ±5%, and especially preferably within ±3%. The lower limit of the variation in acetic acid space time yield is ±0%, but the variation is generally ±0.001% or more. Assume that the variation in acetic acid space time yield in the reactor(s) in operation falls within ±40% between before and after switchover to increase or decrease in number of reactors in operation. The meaning of this is similar to that in the variation in the metal catalyst concentration.

Since the reaction rate and the space time yield are equivalent to each other, the variation in reaction rate in the reactor(s) in operation in the condition (vi) is generally the same value (coefficient of variation) as with the variation in acetic acid space time yield in the reactor(s) in operation in the condition (vii).

The production method according to the present invention may meet at least one of the conditions (i) to (vii), but may meet two or more of the conditions together. Examples of combinations of two or more conditions preferably to be met together include the combinations of conditions of: (i) and (ii); (i) and (iii); (i) and (iv); (i) and (v); (i) and (vi); (i) and (vii); (ii) and (iii); (ii) and (iv); (ii) and (v); (ii) and (vi); (ii) and (vii); (iii) and (iv); (iii) and (v); (iii) and (vi); (iii) and (vii); (iv) and (v); (iv) and (vi); (iv) and (vii); (v) and (vi); (v) and (vii); (vi) and (vii); (i), (ii), and (iii); (i), (ii), and (iv); (i), (ii), and (v); (i), (ii), and (vi); (i), (ii), and (vii); (i), (iii), and (iv); (i), (iii), and (v); (i), (iii), and (vi); (i), (iii), and (vii); (i), (iv), and (v); (i), (iv), and (vi); (i), (iv), and (vii); (i), (v), and (vi); (i), (v), and (vii); (ii), (iii), and (iv); (ii), (iii), and (v); (ii), (iii), and (vi); (ii), (iii), and (vii); (ii), (iv), and (v); (ii), (iv), and (vi); (ii), (iv), and (vii); (iii), (iv), and (v); (iii), (iv), and (vi); (iii), (iv), and (vii); (i), (ii), (iii), and (iv); (i), (ii), (iii), and (v); (i), (ii), (iii), and (vi); (i), (ii), (iii), and (vii); (i), (iii), (iv), (v), and (vi); (ii), (iii), (iv), (v), and (vi); and (i), (ii), (iii), (iv), (v), (vi), and (vii). Among them, it is particularly preferred that the method meets at least the conditions (i), (ii), and (iii) together; at least the conditions (i), (ii), (iii), and (iv) together; or all the conditions (i), (ii), (iii), (iv), (v), (vi), and (vii) together.

Assume that the reactors 1A and 1B are used in parallel as illustrated in FIG. 1, and the acetic acid production volume is to be reduced to half the regular production volume. In this case, the acetic acid production volume is reduced typically by reducing the amounts of the starting material methanol and the starting material carbon monoxide individually to half in the entire process, and operating only one of the reactors 1A and 1B (half load). Even when the operation is switched over to one-reactor operation as above, namely, even when the charge amounts are reduced to half by reducing the number of reactors in operation, the variations can be restrained, because the reaction mixture composition in the reactor is approximately the same as in the two-reactor operation (full load). For the same reason, the hydrogen partial pressure, the reaction temperature, the reaction rate, and the space time yield in each reactor are held within specific ranges, and significant variations in these parameters are restrained. The configuration advantageously eliminates the need typically for lowering the catalyst concentration in the reactor by adjusting the liquid level (namely, by raising the liquid level) in the evaporator in order to recycle a solution of the metal catalyst in a lower concentration.

The second acetic acid production method is an acetic acid production method that includes a carbonylation step. In the carbonylation step, methanol is reacted with carbon monoxide in a continuous system in the presence of a catalytic system, acetic acid, methyl acetate, and water, where the catalytic system includes a metal catalyst and methyl iodide.

In the carbonylation step, a variation in acetic acid space time yield is held within ±40% upon reduction of the acetic acid production volume down to 30% to 90%.

The second acetic acid production method may employ two or more reactors disposed in parallel, and the acetic acid production volume may be reduced by reducing the number of working reactor.

For example, the method can hold the space time yield within a specific range approximate to that in full load operation, even when the acetic acid production volume reduced to 30% to 90% (e.g., 35%, 40%, 45%, 50%, 55%, 60%, 65%, 70%, 75%, 80%, or 85%) by increasing or decreasing the number of reactors in operation, of the two or more parallel reactors. The variation in space time yield is typically within ±40%, within ±35%, within ±30%, within ±25%, preferably within ±15%, more preferably within ±10%, furthermore preferably within ±8%, particularly preferably within ±5%, and especially preferably within ±3%. The lower limit of the variation in space time yield is ±0%, but the variation is generally 0.001% or more. The acetic acid space time yield in the reaction system may be typically about 5 to about 50 mol/L·h, preferably about 8 to about 40 mol/L·h, and furthermore preferably about 10 to about 30 mol/L·h.

The condenser 1a cools and partially condenses the vapors from the reactors 1A and/or 1B to separate the vapors into condensates and gases. The condensates typically include methyl iodide, hydrogen iodide, water, methyl acetate, acetic acid, dimethyl ether, methanol, acetaldehyde, formic acid, and propionic acid. The condensates are introduced and recycled from the condenser 1a through the line 14 to the reactors 1A and/or 1B. The gases typically include carbon monoxide, hydrogen, methane, carbon dioxide, nitrogen, oxygen, methyl iodide, hydrogen iodide, water, methyl acetate, acetic acid, dimethyl ether, methanol, acetaldehyde, and formic acid. The gases are fed from the condenser 1a through the line 15 to the scrubbing system 8. In the scrubbing system 8, useful components (such as methyl iodide, water, methyl acetate, and acetic acid) are separated and recovered from the gases fed from the condenser 1a. In the embodiment, the separation and recovery employs a wet process using an absorbing liquid (absorbent) for collecting useful components from the gases. The absorbing liquid is preferably selected from absorbing solvents containing at least one of acetic acid and methanol. The absorbing liquid may contain methyl acetate. For example, condensates derived from vapors from the after-mentioned distillation column 6 are usable as the absorbing liquid. The separation and recovery may employ a pressure swing adsorption process. The separated, recovered useful components (such as methyl iodide) are introduced and recycled from the scrubbing system 8 through the recycle line 48 to the reactors 1A and/or 1B. Residual gases after the collection of useful components are discarded through the line 49. In this connection, the gases discharged from the line 49 can be used as a carbon monoxide (CO) source to be introduced into the bottom of the after-mentioned evaporator 2, or into the residue recycle lines 18 and 19. The treatment in the scrubbing system 8, the subsequent recycling to the reactors 1A and/or 1B, and the discarding are also applicable to after-mentioned gases fed from other condensers to the scrubbing system 8. The production method according to the present invention preferably includes a scrubbing step by which an offgas from the process is subjected to an absorbing treatment with an absorbing solvent containing acetic acid, to separate the offgas into a carbon monoxide-rich stream and an acetic acid-rich stream.

In the reactors 1A and/or 1B during operation, acetic acid is continuously formed, as described above. A reaction mixture containing acetic acid as above is drawn from the reactors 1A and/or 1B continuously at a predetermined flow rate and introduced through the line 16 into the subsequent (downstream) evaporator 2.

The evaporator 2 is a unit with which the evaporation step (flash step) is performed. The evaporation step is the step of partially evaporating the reaction mixture so as to separate the reaction mixture into a vapor stream (volatile phase) and a residue stream (low volatile phase; residual liquid stream), where the reaction mixture is continuously introduced through the line 16 (reaction mixture feed line) into the evaporator 2. The evaporation may be performed by reducing the pressure with or without heating. In the evaporation step, the vapor stream temperature is typically 100° C. to 260° C., and preferably 120° C. to 200° C.; the residue stream temperature is typically 80° C. to 200° C., and preferably 100° C. to 180° C.; and the evaporator internal pressure is typically 50 to 1000 kPa (absolute pressure). The ratio of the vapor stream to the residue stream, which are separated from each other in the evaporation step, is typically from 10:90 to 50:50 in terms of mass ratio.

The vapors formed in the step typically include methyl iodide, hydrogen iodide, water, methyl acetate, acetic acid, dimethyl ether, methanol, acetaldehyde, crotonaldehyde, 2-ethylcrotonaldehyde, butyl acetate, formic acid, and propionic acid; as well as alkyl iodides such as ethyl iodide, propyl iodide, butyl iodide, hexyl iodide, and decyl iodide. The vapors are continuously drawn from within the evaporator 2 to the line 17 (vapor stream discharge line). Of the vapor stream drawn from within the evaporator 2, a portion is continuously introduced into the condenser 2a, and another portion is continuously introduced through the line 21 into the subsequent (downstream) distillation column 3. The vapor stream has an acetic acid concentration of typically 40 to 85 mass percent (preferably 50 to 85 mass percent), and furthermore preferably 50 to 75 mass percent (e.g., 55 to 75 mass percent); a methyl iodide concentration of typically 2 to 50 mass percent (preferably 5 to 30 mass percent); a water concentration of typically 0.2 to 20 mass percent (preferably to 15 mass percent); and a methyl acetate concentration of typically 0.2 to 50 mass percent (preferably 2 to 30 mass percent).

The residue stream formed in the step includes the catalyst and the promoter (such as methyl iodide and/or lithium iodide) which have been contained in the reaction mixture; and water, methyl acetate, acetic acid, crotonaldehyde, 2-ethylcrotonaldehyde, butyl acetate, formic acid, propionic acid, and other substances that remain without volatilization in the step. The residue stream is continuously introduced from the evaporator 2 through the line 18 into the heat exchanger 2b, using the pump 57. The heat exchanger 2b cools the residue stream from the evaporator 2. The cooled residue stream is continuously introduced and recycled from the heat exchanger 2b through the line 19 to the reactors 1A and/or 1B. The line 18 and the line 19 are collectively referred to as a "residue stream recycle line(s)". The residue stream has an acetic acid concentration of typically 55 to 90 mass percent, and preferably 60 to 85 mass percent.

The carbon monoxide-containing gas inlet line 54 is preferably coupled to the bottom portion of the evaporator 2 and/or the residue stream recycle line (line 18 and/or line 19), so as to introduce a carbon monoxide-containing gas. Introduction of carbon monoxide to a residue (residual liquid) accumulated in the bottom or lower part of the evaporator 2 and/or to the residue stream passing through the residue stream recycle line 18 and/or 19 (in particular, the line 18) carbon monoxide to be dissolved in a larger amount in the residue stream, thereby allows the catalyst to be more stable, and can protect the catalyst from sedimentation and accumulation. The carbon monoxide-containing gas to be introduced has a carbon monoxide content of typically 10 mass percent or more, preferably 20 mass percent or more, furthermore preferably 40 mass percent or more, and particularly preferably 60 mass percent or more.

In an embodiment, the first acetic acid production method may further include, in addition to the carbonylation step, an evaporation step in which a reaction mixture from the carbonylation step is separated, using an evaporator, into a vapor stream and a residue stream, where the evaporator includes two or more evaporators disposed in parallel and coupled respectively to the two or more parallel reactors. In other words, two or more combinations of a reactor and an evaporator coupled to each other may be used in parallel when the evaporation step is employed.

Assume that two or more reactors are used in parallel, but only one evaporator is used and coupled to the two or more reactors. In this case, the operation of the evaporator may become unstable with variations typically in pressures and flow rates of process streams introduced from the individual reactors into the evaporator. The use of two or more combinations of a reactor coupled to an evaporator in parallel allows the operation to be more stable. As used herein, the term "process stream" refers to a liquid phase or gas phase (vapor phase) in a step for a process unit operation, or in an apparatus or facility with which the process unit operation is performed. Non-limiting examples of the process unit operation include reaction, evaporation, distillation, cooling, condensation, liquid-liquid separation, storage, and absorption, in the acetic acid production equipment. Non-limiting examples of the process stream include liquid phases or gas phases typically in pipes, reactors, evaporators, and distillation columns.

In an embodiment, the first acetic acid production method may further include, in addition to the carbonylation step, an evaporation step and a light ends-removing step. In the evaporation step, a reaction mixture from the carbonylation step is separated, using an evaporator, into a vapor stream and a residue stream. In the light ends-removing step, the vapor stream is separated, by distillation using a distillation column, into an overhead stream rich in at least one light end selected from methyl iodide and acetaldehyde, and an acetic acid stream rich in acetic acid, and the overhead stream is subjected sequentially to condensation and to liquid-liquid separation using two or more decanters, to give an aqueous phase and an organic phase. In the embodiment, the evaporator includes two or more evaporators disposed in parallel and coupled respectively to the two or more parallel reactors, and the distillation column includes two or more distillation columns disposed in parallel and coupled respectively to the two or more parallel evaporators. This configuration is provided so as to correspond to or adapt to load variations typically in pressure and/or flow rate of the process streams as much as possible, which load variations propagate to or affect the light ends columns (first distillation columns) with which the light ends-removing step (first distillation step) is performed.

The configuration allows the operation to be furthermore stable. Columns (facilities) for use in downstream steps do not always have to be provided as two or more columns disposed in parallel and used in combination respectively with the two or more parallel light ends columns. Non-limiting examples of the downstream steps include the dehydration step (second distillation step), the heavy ends-removing step (third distillation step), the aldehyde-removing step, the adsorptive removing step, and the absorption step. This is because acetic acid has been highly purified in such downstream steps, and the acetic acid production is not so significantly affected typically by variations in process conditions and variations in amounts of formed impurities.

In another embodiment, the first acetic acid production method may further include, in addition to the carbonylation step, an evaporation step in which a reaction mixture from the carbonylation step is separated, using an evaporator, into a vapor stream and a residue stream. In this evaporation step, a liquid volume in the evaporator is 1 to 100 parts by volume per 100 parts by volume of the total liquid volume in the parallel reactors, where, when the evaporator includes two or more evaporators disposed in parallel, the term "liquid volume in the evaporator" is read as "total liquid volume in the two or more evaporators".

In a preferred embodiment, the liquid volume in the evaporator may be typically 1 to 100 parts by volume, preferably 1 to 70 parts by volume, more preferably 1 to 50 parts by volume, furthermore preferably 1 to 30 parts by volume, particularly preferably 1 to 20 parts by volume, and especially preferably 1 to 10 parts by volume, per 100 parts by volume of the total liquid volume in the parallel reactors, where, when the evaporator includes two or more evaporators disposed in parallel, the term "liquid volume in the evaporator" is read as "total liquid volume in the two or more evaporators". The capacity of the evaporator(s) may be small to such a degree as not to cause a large variation in liquid level, because, in the evaporator(s), carbon monoxide is present in the gas phase at a very low partial pressure, is dissolved in the liquid (liquid phase) in a very small amount, and thereby hardly undergoes a reaction in the evaporator(s). Such a small liquid volume is rather advantageous, because the sedimentation of the catalyst due to such a low carbon monoxide concentration in the evaporator liquid phase is more restrained with a decreasing liquid volume.

The condenser 2a cools and partially condenses the vapor stream from the evaporator 2 to separate the vapor stream into condensates and gases. The condensates typically include methyl iodide, hydrogen iodide, water, methyl acetate, acetic acid, dimethyl ether, methanol, acetaldehyde, crotonaldehyde, 2-ethylcrotonaldehyde, butyl acetate, formic acid, and propionic acid. The condensates are introduced and recycled from the condenser 2a through the lines 22 and 23 to the reactors 1A and/or 1B. The gases typically include carbon monoxide, hydrogen, methane, carbon dioxide, nitrogen, oxygen, methyl iodide, hydrogen iodide, water, methyl acetate, acetic acid, dimethyl ether, methanol, acetaldehyde, and formic acid. The gases are fed from the condenser 2a through the lines 20 and 15 to the scrubbing system 8. The acetic acid formation reaction in the reaction step is an exothermic reaction. In the evaporation step (flash step), a portion of heat accumulated in the reaction mixture is transferred to the vapors derived from the reaction mixture. The vapors are cooled in the condenser 2a to give condensates, and the condensates are recycled to the reactors 1A and/or 1B. Specifically, this acetic acid production equipment enables efficient removal of heat by the working of the condenser 2a, where the heat is generated in the methanol-carbonylation reaction.

The distillation column 3 is a unit with which the first distillation step is performed. The distillation column 3 in the embodiment is characterized as a so-called ends column. The first distillation step is the step of subjecting the vapor stream, which is continuously introduced into the distillation column 3, to a distillation treatment so as to separate and remove light ends therefrom. More specifically, the first distillation step is the step of separating, by distillation, the vapor stream into an overhead stream rich in at least one light end selected from methyl iodide and acetaldehyde, and an acetic acid stream rich in acetic acid. The distillation column 3 may be selected typically from rectification columns such as a plate column and a packed column. The distillation column 3 when being a plate column, typically has 5 to 50 theoretical plates, and is operated at a reflux ratio of typically 0.5 to 3000, where the reflux ratio may be determined according to the number of theoretical plates. In the distillation column 3, the column top pressure is set typically to 80 to 160 kPa (gauge pressure); and the column bottom pressure is set to a pressure which is higher than the column top pressure and is typically 85 to 180 kPa (gauge pressure). In the distillation column 3, the column top temperature is set typically to a temperature which is lower than the boiling point of acetic acid at the set column top pressure and is from 90° C. to 130° C.; and the column bottom temperature is set typically to a temperature which is equal to or higher than the boiling point of acetic acid at the set column bottom pressure and is from 120° C. to 160° C.

At the distillation column 3, the vapor stream from the evaporator 2 is continuously introduced through the line 21; vapors as an overhead stream are continuously drawn from a column top portion to the line 24; and bottoms are continuously drawn from a column bottom portion to the line 25. There is disposed the reboiler 3b. An acetic acid stream (first acetic acid stream; liquid) as a side stream is continuously drawn, through the line 27, from the distillation column 3 at a height position between the column top and the column bottom.

The vapors drawn from the column top portion of the distillation column 3 include larger amounts of light ends as compared with the bottoms and the side stream from the distillation column 3, and typically include methyl iodide, hydrogen iodide, water, methyl acetate, dimethyl ether, methanol, acetaldehyde, crotonaldehyde, and formic acid, where the light ends are components having lower boiling points as compared with acetic acid. The vapors also include acetic acid. The vapors as above are continuously introduced through the line 24 into the condenser 3a.

The condenser 3a cools and partially condenses the vapors from the distillation column 3 to separate the vapors into condensates and gases. The condensates typically include methyl iodide, hydrogen iodide, water, methyl acetate, acetic acid, dimethyl ether, methanol, acetaldehyde, crotonaldehyde, and formic acid. The condensates are continuously introduced from the condenser 3a through the line 28 into the decanter 4. The condensates introduced into the decanter 4 are liquid-liquid separated into an aqueous phase (upper phase) and an organic phase (methyl iodide phase; lower phase). The aqueous phase includes water, and other components such as methyl iodide, hydrogen iodide, methyl acetate, acetic acid, dimethyl ether, methanol, acetaldehyde, crotonaldehyde, and formic acid. The organic phase typically includes methyl iodide, and other components such as hydrogen iodide, water, methyl acetate, acetic acid, dimethyl ether, methanol, acetaldehyde, crotonaldehyde, and formic acid. In the embodiment, of the aqueous phase, a portion is refluxed through the line 29 to the distillation column 3; and another portion is introduced through the lines 29, 30, and 51 into the acetaldehyde-removing system 9, in which acetaldehyde is separated and removed through the line 53 out of the system. The resulting residual liquid after removal of acetaldehyde recycled through the lines 52 and 23 to the reactors 1A and/or 1B. Yet another portion of the aqueous phase may be recycled through the lines 29, 30, and 23 to the reactors 1A and/or 1B without passing through the acetaldehyde-removing system 9. The organic phase is introduced and recycled through the line 31 and 23 to the reactors 1A and/or 1B. A portion of the organic phase may be introduced through the lines 31 and 50 into the acetaldehyde-removing system 9, as needed. In addition to or instead of refluxing of the aqueous phase to the distillation column 3, the organic phase may be refluxed to the distillation column 3.

In another embodiment, the first acetic acid production method may further include, in addition to the carbonylation step, an evaporation step and a light ends-removing step. In the evaporation step, a reaction mixture from the carbonylation step is separated, using an evaporator, into a vapor stream and a residue stream. In the light ends-removing step, the vapor stream is separated, by distillation using a distillation column, into an overhead stream rich in at least one light end selected from methyl iodide and acetaldehyde, and an acetic acid stream rich in acetic acid, and the overhead stream is subjected sequentially to condensation and to liquid-liquid separation using a decanter to give an aqueous phase and an organic phase. In the light ends-removing step, a liquid volume in the decanter is 1 to 100 parts by volume per 100 parts by volume of the total liquid volume in the parallel reactors, where, when the decanter includes two or more decanters disposed in parallel, the term "liquid volume in the decanter" is read as "total liquid volume in the two or more decanters".

In a preferred embodiment, the liquid volume in the decanter may be typically 1 to 100 parts by volume, and is preferably 1 to 70 parts by volume, more preferably 1 to 50 parts by volume, furthermore preferably 1 to 30 parts by volume, particularly preferably 1 to 20 parts by volume, and especially preferably 1 to 10 parts by volume, per 100 parts by volume of the total liquid volume in the parallel reactors, where, when the decanter includes two or more decanters disposed in parallel, the term "liquid volume in the decanter" is read as "total liquid volume in the two or more decanters". To restrain increase in installation cost, the capacity of the decanter(s) is preferably small to such a degree as to enable stable operation of the corresponding column by maintaining the variation in liquid level to a specific level or lower. However, such a small capacity of the decanter(s) may impede the increase and/or decrease of the amount of the organic phase in the decanter(s) and thereby limit the adjustment of the reaction rate in the reactor(s) when the methyl iodide concentration in the reactor(s) is to be adjusted.

In yet another embodiment, the first acetic acid production method may further include, in addition to the carbonylation step, an evaporation step and a light ends-removing step. In the evaporation step, a reaction mixture from the carbonylation step is separated, using an evaporator or evaporators, into a vapor stream and a residue stream. In the light ends-removing step, the vapor stream is separated, by distillation, into an overhead stream rich in at least one light end selected from methyl iodide and acetaldehyde, and an acetic acid stream rich in acetic acid; and the overhead stream is subjected sequentially to condensation and to liquid-liquid separation using a decanter or decanters, to give an aqueous phase and an organic phase.

In the embodiment, during operation with increase or decrease in number of reactors in operation, the reactor(s) in operation is operated at a reaction temperature of 170° C. or higher, and at least one of conditions (viii) to (x) is met regardless of the number of reactors in operation, where the conditions (viii) to (x) are expressed as follows:

(viii) a variation in liquid level in the reactor(s) in operation falls within ±20%;

(ix) a variation in liquid level in the working evaporator(s) falls within ±20%; and (x) a variation in liquid level in the working decanter(s) falls within ±20%.

The variations are observed for a period of typically 5 days, 10 days, 30 days, half a year, or one year.

The method may meet at least one of the conditions (viii) to (x) between before and after switchover to increase or decrease in number of reactors in operation.

As used herein, the term "variation" between before and after switchover to increase or decrease in number of reactors in operation refers to a variation of the average of parameter values over a predetermined period (e.g., 5 days, 10 days, 30 days, half a year, or one year) after switchover to increase or decrease, relative to the average of parameter values over a predetermined period (5 days, 10 days, 30 days, half a year, or one year) before switchover to increase or decrease.

For example in the embodiment illustrated in FIG. 1, a non-limiting example of the switchover to increase or decrease in number of reactors in operation is the case where only the reactor 1A is operated after both the reactors 1A and/or 1B are operated. In this case, assume that a variation in liquid level in the reactor(s) in operation falls within ±20% between before and after switchover to increase or decrease in number of reactors in operation. This means that the variation in liquid level in the reactor 1A after switchover of number of reactors in operation falls within ±20% relative to the liquid level in the reactor 1A and the liquid level in the reactor 1B before switchover of number of reactors in operation. Before switchover of number of reactors in operation, the liquid level in the reactor 1A is approximately identical to the liquid level in the reactor 1B. This is probably also true for the variations in the working evaporator(s) and the working decanter(s) between before and after switchover to increase or decrease in number of reactors in operation.

Relating to the condition (viii), the variation in liquid level in the reactor(s) in operation is typically within ±20%, preferably within ±15%, more preferably within ±10%, furthermore preferably within ±8%, particularly preferably within ±5%, and especially preferably within ±3%. The lower limit of the variation in liquid level in the reactor(s) in operation is ±0%, but the variation is generally 0.001% or more. In the acetic acid production method according to the present invention, the liquid level in the reactor(s) in operation does not significantly vary regardless of the number of reactors in operation. This allows the metal catalyst and the promoter to be present in the reaction system at constant levels and enables stable and efficient operation.

Relating to the condition (ix), the variation in liquid level in the working evaporator(s) is typically within ±20%, preferably within ±15%, more preferably within ±10%, furthermore preferably within ±8%, particularly preferably within ±5%, and especially preferably within ±3%. The lower limit of the variation in liquid level in the working evaporator(s) is ±0%, but the variation is generally 0.001% or more. In the acetic acid production method according to the present invention, the liquid level in the working evaporator(s) does not significantly vary regardless of the number of reactors in operation. This enables stable and efficient operation.

Relating to the condition (x), the variation in liquid level in the working decanter(s) is typically within ±20%, preferably within ±15%, more preferably within ±10%, furthermore preferably within ±8%, particularly preferably within ±5%, and especially preferably within ±3%. The lower limit of the variation in liquid level in the working decanter(s) is ±0%, but the variation is generally 0.001% or more. In the acetic acid production method according to the present invention, the liquid level in the working decanter(s) does not significantly vary regardless of the number of reactors in operation. This enables stable and efficient operation. As used herein, the term "liquid level" in the working decanter(s) refers to the liquid level of an organic phase, of an aqueous phase (upper phase) and the organic phase (methyl iodide phase; lower phase) both of which phases are liquid-liquid separated from each other.

To reduce acetic acid production according to conventional techniques, the liquid level in the reactor, the evaporator, or the decanter is raised to adjust the amounts of the metal catalyst and the promoter to be recycled into the reactor. However, the advantageous effect of liquid level adjustment in a continuous process is only little, and the catalyst concentration in the reactor could by reduced by only about one tenth. In addition, the capacities of the reactor, the evaporator, and the methyl iodide reservoir (such as a decanter) is designed to be larger, by only about one tenth, than the scales corresponding to the planed acetic acid production volume, from the viewpoint of optimizing the installation cost.

Accordingly, such techniques depending only on the adjustment of liquid level have a limitation in adjustment of the acetic acid production volume, and may disadvantageously invite unstable operation in the continuous process. In contrast, the acetic acid production methods according to the present invention, which do not depend on liquid level adjustment, enable stable and efficient continuous operation, even when the acetic acid production volume changed.

The first acetic acid production method may meet at least one of the conditions (viii) to (x), but may meet two or more of the conditions together. Examples of preferred combinations of two or more conditions to be met together include the combinations of conditions of: (viii) and (ix); (ix) and (x); (viii) and (x); and (viii), (ix), and (x). Among them, it is particularly preferred that at least the conditions (viii) and (ix) are met together; or all the conditions (viii), (ix), and (x) are met together.

The acetaldehyde-removing step using the acetaldehyde-removing system 9 removes acetaldehyde from at least one of the organic phase and the aqueous phase by a known technique such as distillation, or extraction, or both in combination. The separated acetaldehyde is discharged through the line 53 out of the equipment. Useful components (such as methyl iodide) contained in at least one of the organic phase and the aqueous phase are recycled through the lines 52 and 23 to the reactors 1A and/or 1B.

FIG. 2 depicts a schematic flow chart according to an embodiment, in which two reactors are disposed in parallel and coupled respectively to two evaporators disposed in parallel. In this embodiment, the reactor 1A is coupled to an evaporator 2A, and in parallel with this, the reactor 1B is coupled to an evaporator 2B, and these are coupled to one distillation column 3. Other configurations than this are as in the embodiment illustrated in FIG. 1.

FIG. 3 depicts a schematic flow chart according to an embodiment, in which two reactors, two evaporators, and two distillation columns are disposed in parallel and coupled respectively to each other. In this embodiment, the reactor 1A, the evaporator 2A, and a distillation column 3A are coupled to each other, and in parallel with this, the reactor 1B, the evaporator 2B, and a distillation column 3B are coupled to each other. Vapors from the distillation columns 3A and/or 3B are cooled and partially condensed by condensers 3a and/or 3a and are separated into condensates and gases. The condensates typically include methyl iodide, hydrogen iodide, water, methyl acetate, acetic acid, dimethyl ether, methanol, acetaldehyde, crotonaldehyde, and formic acid; and are continuously fed from the two condensers 3a and 3a respectively through the lines 28 and/or 28 into decanters 4A and/or 4B. Other configurations than this are as with the embodiment illustrated in FIG. 1.

Referring back to FIG. 1, the gases formed by the working of the condenser 3a typically include carbon monoxide, hydrogen, methane, carbon dioxide, nitrogen, oxygen, methyl iodide, hydrogen iodide, water, methyl acetate, acetic acid, dimethyl ether, methanol, acetaldehyde, and formic acid. The gases are fed from the condenser 3a through the lines 32 and 15 to the scrubbing system 8. Of the gases that reach the scrubbing system 8, components such as methyl iodide, hydrogen iodide, water, methyl acetate, acetic acid, dimethyl ether, methanol, acetaldehyde, and formic acid are absorbed by the absorbing liquid in the scrubbing system 8. Hydrogen iodide reacts with methanol or methyl acetate in the absorbing liquid to form methyl iodide. The resulting liquid containing the methyl iodide and other useful components is recycled from the scrubbing system 8 through the recycle lines 48 and 23 to the reactors 1A and/or 1B.

The bottoms drawn from the column bottom portion of the distillation column 3 include larger amounts of heavy ends as compared with the overhead stream and the side stream from the distillation column 3, and typically include propionic acid, as well as the catalyst and the promoter as being entrained, where heavy ends are components having higher boiling points as compared with acetic acid. The bottoms also include other components such as acetic acid, methyl iodide, methyl acetate, crotonaldehyde, 2-ethylcrotonaldehyde, butyl acetate, and water. In the embodiment, of the bottoms as above, a portion is continuously introduced through the lines 25 and 26 to the evaporator 2; and another portion is continuously introduced and recycled through the lines 25 and 23 to the reactors 1A and/or 1B.

The first acetic acid stream, which is continuously drawn as a side stream from the distillation column 3, is enriched with acetic acid as compared with the vapor stream continuously introduced into the distillation column 3. Specifically, the acetic acid concentration in the first acetic acid stream is higher than the acetic acid concentration in the vapor stream. The acetic acid concentration in the first acetic acid stream is typically 90 to 99.9 mass percent, and preferably 93 to 99 mass percent. The first acetic acid stream includes not only acetic acid, but also other components such as methyl iodide, hydrogen iodide, water, methyl acetate, dimethyl ether, methanol, acetaldehyde, crotonaldehyde, 2-ethylcrotonaldehyde, butyl acetate, formic acid, and propionic acid, as well as alkyl iodides such as ethyl iodide, propyl iodide, butyl iodide, hexyl iodide, and decyl iodide. The first acetic acid stream has a methyl iodide concentration of typically 0.1 to 8 mass percent, and preferably 0.2 to 5 mass percent; a water concentration of typically 0.1 to 8 mass percent, and preferably 0.2 to 5 mass percent; and a methyl acetate concentration of typically 0.1 to 8 mass percent, and preferably 0.2 to 5 mass percent.

The line 27 may be coupled to the distillation column 3 at a height higher than the coupling height of the line 21 to the distillation column 3 as illustrated in the figure, but may also be coupled at a height lower than or equal to the coupling height of the line 21 to the distillation column 3. The first acetic acid stream from the distillation column 3 is introduced through the line 27 into the subsequent (downstream) distillation column 5 continuously at a predetermined flow rate. The first acetic acid stream drawn as a side stream from the distillation column 3, the bottoms from the distillation column 3, or a condensate derived from vapors in the column bottom portion of the distillation column 3 may be used as intact as an acetic acid product, or may be continuously introduced directly into the distillation column 6 without passing through the distillation column 5. The line 27 and the distillation column 5 (at least a portion which comes in contact with a liquid or gas) may be made of a stainless steel, but are preferably made of a highly corrosion resistant metal such as a nickel base alloy or zirconium, so as to restrain corrosion of the interior of pipes, where the corrosion will be caused by hydrogen iodide and/or acetic acid.

To the first acetic acid stream flowing through the line 27, potassium hydroxide may be fed or added through the line 55 (potassium hydroxide inlet line). The potassium hydroxide may be fed or added typically as a solution such as an aqueous solution. The feeding or addition of potassium hydroxide to the first acetic acid stream can decrease hydrogen iodide in the first acetic acid stream. Specifically, hydrogen iodide reacts with potassium hydroxide to form potassium iodide and water. This can decrease hydrogen iodide-induced corrosion of the equipment such as distillation columns. In this process, potassium hydroxide can be fed or added to an appropriate site where hydrogen iodide is present. The potassium hydroxide added in the process also reacts with acetic acid to form potassium acetate.

The distillation column 5 is a unit with which the second distillation step is performed. The distillation column 5 in the embodiment is characterized as a so-called dehydration column. The second distillation step is the step of subjecting the first acetic acid stream, which is continuously introduced into the distillation column 5, to a distillation treatment so as to further purify acetic acid. The distillation column 5 is selected from rectification columns such as a plate column and a packed column. The distillation column 5, when being a plate column, has 5 to 50 theoretical plates and is operated at a reflux ratio of typically 0.2 to 3000, where the reflux ratio may be determined according to the number of theoretical plates. In the distillation column 5 during the second distillation step, the column top pressure is set typically to 150 to 250 kPa (gauge pressure); and the column bottom pressure is set to a pressure which is higher than the column top pressure and is typically 160 to 290 kPa (gauge pressure). In the distillation column 5 during the second distillation step, the column top temperature is set typically to a temperature which is higher than the boiling point of water but lower than the boiling point of acetic acid at the set column top pressure and is from 130° C. to 160° C.; and the column bottom temperature is set typically to a temperature which is equal to or higher than the boiling point of acetic acid at the set column bottom pressure and is from 150° C. to 175° C.

At the distillation column 5, vapors as an overhead stream are continuously drawn from a column top portion to the line 33; and bottoms are continuously drawn from a column bottom portion to the line 34. There is disposed the reboiler 5b. A side stream (liquid or gas) may be continuously drawn, to the line 34, from the distillation column 5 at a height position between the column top and the column bottom.

The vapors drawn from the column top portion of the distillation column 5 include larger amounts of light ends as compared with the bottoms from the distillation column 5, and typically include methyl iodide, hydrogen iodide, water, methyl acetate, acetic acid, dimethyl ether, methanol, acetaldehyde, crotonaldehyde, and formic acid, where the light ends are components having lower boiling points as compared with acetic acid. The vapors as above are continuously introduced through the line 33 into the condenser 5a.

The condenser 5a cools and partially condenses the vapors from the distillation column 5 to separate the vapors into condensates and gases. The condensates typically include water and acetic acid. Of the condensates, a portion is continuously refluxed from the condenser 5a through the line 35 to the distillation column 5; and another portion is introduced and recycled from the condenser 5a through the lines 35, 36, and 23 to the reactors 1A and/or 1B. The gases from the condenser 5a typically include carbon monoxide, hydrogen, methane, carbon dioxide, nitrogen, oxygen, methyl iodide, hydrogen iodide, water, methyl acetate, acetic acid, dimethyl ether, methanol, acetaldehyde, and formic acid. The gases are fed from the condenser 5a through the lines 37 and 15 to the scrubbing system 8. Hydrogen iodide in the gases that reach the scrubbing system 8 is absorbed by the absorbing liquid in the scrubbing system 8 and, in the absorbing liquid, reacts with methanol or methyl acetate to give methyl iodide. The resulting liquid containing the methyl iodide and other useful components is recycled from the scrubbing system 8 through the recycle lines 48 and 23 to the reactors 1A and/or 1B.

The bottoms drawn from the column bottom portion of the distillation column 5 (or a side stream from this column) include larger amounts of heavy ends as compared with the overhead stream from the distillation column 5 and typically include propionic acid, potassium acetate (when potassium hydroxide is fed typically to the line 27), and the catalyst and the promoter as being entrained, where the heavy ends are components having higher boiling points as compared with acetic acid. The bottoms may also include acetic acid. The bottoms as above are continuously introduced, as a second acetic acid stream, through line 34 into the subsequent (downstream) distillation column 6.

The second acetic acid stream is enriched with acetic acid as compared with the first acetic acid stream continuously introduced into the distillation column 5, where the second acetic acid stream is the bottoms or the side stream drawn respectively from the column bottom portion or a portion of the distillation column 5 at an intermediate height. Specifically, the acetic acid concentration in the second acetic acid stream is higher than the acetic acid concentration in the first acetic acid stream. The acetic acid concentration in the second acetic acid stream is typically 99.1 to 99.99 mass percent, as long as being higher than the acetic acid concentration in the first acetic acid stream. The second acetic acid stream may further include, in addition to acetic acid, other components such as propionic acid and hydrogen iodide, as described above. In the embodiment, the side stream, when to be drawn, is drawn from the distillation column 5 at a height lower than the height at which the first acetic acid stream is introduced into the distillation column 5.

To the second acetic acid stream flowing through the line 34, potassium hydroxide may be fed or added through the line 56 (potassium hydroxide inlet line). Potassium hydroxide may be fed or added as a solution such as an aqueous solution. The feeding or addition of potassium hydroxide to the second acetic acid stream can decrease the amount of hydrogen iodide in the second acetic acid stream. Specifically, hydrogen iodide reacts with potassium hydroxide to form potassium iodide and water. This reduces hydrogen iodide-induced corrosion of the equipment such as distillation columns.

The distillation column 6 is a unit with which the third distillation step is performed. The distillation column 6 in the embodiment is characterized as a so-called heavy ends column. The third distillation step is the step of subjecting the second acetic acid stream, which is continuously introduced into the distillation column 6, to purification treatment so as to further purify acetic acid. This step is not indispensable in the embodiment. The distillation column 6 may be selected typically from rectification columns such as a plate column and a packed column. The distillation column 6, when being a plate column, typically has 5 to 50 theoretical plates and is operated at a reflux ratio of typically 0.2 to 3000, where the reflux ratio may be determined according to the number of theoretical plates. In the distillation column 6 during the third distillation step, the column top pressure is set typically to −100 to 150 kPa (gauge pressure); and the column bottom pressure is set to a pressure which is higher than the column top pressure and is typically from −90 to 180 kPa (gauge pressure). In the distillation column 6 during the third distillation step, the column top temperature is set typically to a temperature which is higher than the boiling point of water and lower than the boiling point of acetic acid at the set column top pressure and is from 50° C. to 150° C.; and the column bottom temperature is set typically to a temperature which is higher than the boiling point of acetic acid at the set column bottom pressure and is from 70° C. to 160° C.

At the distillation column 6, vapors as an overhead stream are continuously drawn from a column top portion to the line 38; and bottoms are continuously drawn from a column bottom portion to the line 39. There is disposed the reboiler 6b. A side stream (liquid or gas) is continuously drawn, to the line 46, from the distillation column 6 at a height position between the column top and the column bottom. To the distillation column 6, the line 46 may be coupled at a height higher than the coupling height of the line 34 to the distillation column 6, as illustrated in the figure, but may be coupled at a height lower than or equal to, the coupling height of the line 34 to the distillation column 6.

The vapors drawn from the column top portion of the distillation column 6 include larger amounts of light ends as compared with the bottoms from the distillation column 6, where the light ends are components having lower boiling points as compared with acetic acid. The vapors include acetic acid; and other components such as methyl iodide, hydrogen iodide, water, methyl acetate, dimethyl ether, methanol, and formic acid. The vapors as above are continuously introduced through the line 38 into the condenser 6a.

The condenser 6a cools and partially condenses the vapors from the distillation column 6 to separate the vapors into condensates and gases. The condensates include acetic acid; and other components such as methyl iodide, hydrogen iodide, water, methyl acetate, dimethyl ether, methanol, and formic acid. At least a portion of the condensates is continuously refluxed from the condenser 6a through the line 40 to the distillation column 6. Another portion of the condensates can be recycled as a distillate from the condenser 6a through the lines 40, 41, and 42 to the first acetic acid stream in the line 27 before introduction into the distillation column 5. In addition to or instead of this, a portion of the condensates can be recycled as a distillate from the condenser 6a through the lines 40, 41, and 43 to the vapor stream in the line 21 before introduction into the distillation column 3. A portion of the condensates may be recycled as a distillate from the condenser 6a through the lines 40, 44, and 23 to the reactors 1A and/or 1B. A portion of the distillate from the condenser 6a can be fed to the scrubbing system 8 and be used as the absorbing liquid in the system, as described above. At the scrubbing system 8, gases from which useful components have been absorptively removed are discharged out of the equipment, whereas the liquid containing the useful components is introduced or recycled from the scrubbing system 8 through the recycle lines 48 and 23 to the reactors 1A and/or 1B. In addition, a portion of the distillate from the condenser 6a may be brought through lines (not shown) to various pumps (not shown) operated in the equipment and be used as a sealing liquid for the pumps. Further, a portion of the distillate from the condenser 6a may be drawn out of the system steadily, or non-steadily at the time of need, through a draw line attached to the line 40. When a portion (distillate) of the condensates is removed from the distillation treatment system in the distillation column 6, the amount of the distillate (distillate amount) is typically 0.01 to 30 mass percent, preferably 0.1 to 10 mass percent, more preferably 0.3 to 5 mass percent, and furthermore preferably 0.5 to 3 mass percent, of the condensates obtained by the working of the condenser 6a. In contrast, the gases formed in the condenser 6a typically include carbon monoxide, hydrogen, methane, carbon dioxide, nitrogen, oxygen, methyl iodide, hydrogen iodide, water, methyl acetate, acetic acid, dimethyl ether, methanol, acetaldehyde, and formic acid. The gases are fed from the condenser 6a through the lines 45 and 15 to the scrubbing system 8.

The bottoms drawn from the column bottom portion of the distillation column 6 through the line 39 include larger amounts of heavy ends as compared with the overhead stream from the distillation column 6, where the heavy ends are components having higher boiling points as compared with acetic acid. The vapors typically include propionic acid, and potassium acetate or another acetate (when potassium hydroxide or another alkali is fed typically to the line 34). The bottoms drawn from the column bottom portion of the distillation column 6 through the line 39 also include metals such as corrosion metals, exemplified by metals liberated from inner walls of constitutional members of the acetic acid production equipment; and compounds between iodine derived from corrosive iodine and the metals such as corrosion metals. In the embodiment, the bottoms as above are discharged out of the acetic acid production equipment.

The side stream continuously drawn from the distillation column 6 to the line 46 is continuously introduced, as a third acetic acid stream, into the subsequent (downstream) ion exchange resin column 7. The third acetic acid stream is enriched with acetic acid as compared with the second acetic acid stream, which is continuously introduced into the distillation column 6. Specifically, the acetic acid concentration in the third acetic acid stream is higher than the acetic acid concentration in the second acetic acid stream. The acetic acid concentration in the third acetic acid stream is typically 99.8 to 99.999 mass percent, as long as being higher than the acetic acid concentration in the second acetic acid stream. In the embodiment, the side stream is drawn from the distillation column 6 at a height higher than the height at which the second acetic acid stream is introduced into the distillation column 6. In another embodiment, the side stream is drawn from the distillation column 6 at a height equal to or lower than the height at which the second acetic acid stream is introduced into the distillation column 6. In place of the distillation column 6, a simple distillator (evaporator) is usable. The distillation column 6 can be omitted when impurities are sufficiently removed.

The ion exchange resin column 7 is a purification unit with which the adsorptive removing step is performed. The adsorptive removing step is the step of removing, by adsorption, mainly alkyl iodides (such as hexyl iodide and decyl iodide) contained in trace amounts in the third acetic acid stream, to further purify acetic acid, where the third acetic acid stream is continuously introduced into the ion exchange resin column 7. In the ion exchange resin column 7, an ion exchange resin capable of adsorbing alkyl iodides is packed and forms an ion exchange resin bed. Non-limiting examples of the ion exchange resin as above include cation-exchange resins with part of leaving protons in exchange groups being substituted or replaced with a metal such as silver or copper, where the exchange groups are exemplified typically by sulfonic groups, carboxy groups, and phosphonate groups. In the adsorptive removing step, the third acetic acid stream (liquid) passes through the inside of the ion exchange resin column 7 packed typically with the ion exchange resin as above, and, during the passing process, alkyl iodides and other impurities are adsorbed and removed from the third acetic acid stream by the ion exchange resin. In the ion exchange resin column 7 during the adsorptive removing step, the internal temperature is typically 18° C. to 100° C., and the acetic acid stream flow rate is typically 3 to 15 m$^3$/h·m$^3$ (resin volume), where the acetic acid stream flow rate is the acetic acid throughput (m$^3$/h) per cubic meter of the resin volume.

From a bottom portion of the ion exchange resin column 7, a fourth acetic acid stream is continuously drawn to the line 47. The fourth acetic acid stream has a higher acetic acid concentration as compared with the third acetic acid stream. Specifically, the fourth acetic acid stream is enriched with acetic acid as compared with the third acetic acid stream, which is continuously introduced into the ion exchange resin column 7. The acetic acid concentration in the fourth acetic acid stream is typically 99.9 to 99.999 mass percent, or more, as long as being higher than the acetic acid concentration in the third acetic acid stream. In the production method, the fourth acetic acid stream can be stored in a product tank (not shown).

This acetic acid production equipment may include a so-called product column or finishing column, which is a distillation column, as a purification unit for further purifying the fourth acetic acid stream from the ion exchange resin column 7. The product column as above, when provided, may be selected typically from rectification columns such as a plate column and a packed column. the product column, when being a plate column, typically has 5 to 50 theoretical plates and is operated at a reflux ratio of typically 0.5 to 3000, where the reflux ratio may be determined according to the number of theoretical plates. In the product column during the purification step, the column top pressure is set typically to −195 to 150 kPa (gauge pressure); and the column bottom pressure is set to a pressure which is higher than the column top pressure and is typically from −190 to 180 kPa (gauge pressure). In the product column, the column top temperature is typically set to a temperature which is higher than the boiling point of water and lower than the boiling point of acetic acid at the set column top pressure and is from 50° C. to 150° C.; and the column bottom temperature is typically set to a temperature which is higher than the boiling point of acetic acid at the set column bottom pressure and is from 70° C. to 160° C. In place of the product column or finishing column, a simple distillator (evaporator) is usable.

Into the product column, when provided, all or a portion of the fourth acetic acid stream (liquid) from the ion exchange resin column 7 is continuously introduced. At the product column as above, vapors as an overhead stream are continuously drawn from a column top portion, where the vapors include trace amounts of light ends such as methyl iodide, water, methyl acetate, dimethyl ether, crotonaldehyde, acetaldehyde, and formic acid. The vapors are separated, using a predetermined condenser, into condensates and gases. Of the condensates, a portion is continuously refluxed to the product column; and another portion may be recycled to the reactors 1A and/or 1B, or be discarded out of the system, or both. The gases are fed to the scrubbing system 8. At the product column, bottoms including trace amounts of heavy ends are continuously drawn from a column bottom portion, and are typically recycled to the second acetic acid stream in the line 34 before introduction into the distillation column 6. At the product column, a side stream (liquid) as a fifth acetic acid stream s continuously drawn from a portion at a height position between the column top and the column bottom. The side stream is drawn from the product column typically at a height lower than the height at which the fourth acetic acid stream is introduced into the product column. The fifth acetic acid stream is enriched with acetic acid as compared with the fourth acetic acid stream, which is continuously introduced into the product column. Specifically, the acetic acid concentration in the fifth acetic acid stream is higher than the acetic acid concentration in the fourth acetic acid stream. The acetic acid concentration in the fifth acetic acid stream is typically 99.9 to 99.999 mass percent, or more, as long as being higher than the acetic acid concentration in the fourth acetic acid stream. The fifth acetic acid stream is stored typically in a product tank (not shown). Instead of or in addition to being disposed downstream from the distillation column 6, the ion exchange resin column 7 may be disposed downstream from the product column, for the treatment of the acetic acid stream from the product column.

EXAMPLES

The present invention will be further illustrated with reference to several examples below. These examples are each on the basis of one exemplary test operation, and compositions and operation conditions to carry out the examples are described with reference to very concrete numerical values. It should be noted, however, that these numerical values are never construed to limit the scope of the present invention. A composition in a system may respond to or be affected by, for example, hydrogen and/or oxygen and may slightly vary. Accordingly, numerical values relating to the examples given in the table represent numerical values each at a certain time point in carrying out.

All parts, percentages, and parts per million (ppm) are by weight. The concentrations were measured by the Karl Fischer method (moisture measurement method) for water; by ICP spectrometry (or atomic absorption spectrometry) for metal ions; and by gas chromatography for other components.

Comparative Example 1

An experiment as follows was performed in a methanol-acetic acid pilot plant according to a continuous system (see FIG. 4).

Into a reactor (capacity: 1 part), 1 part by weight of methanol and 1 part by weight of carbon monoxide were charged at a total pressure of 2.7 MPaG (gauge pressure), followed by carbonylation reaction with the composition given in Table 1. After the reaction, an evaporator, a light ends column, and a dehydration column were operated, and light ends were recycled from the column tops of the ends column and the dehydration column to the reaction system. As a result of measurement, the propionic acid concentration of bottoms from the dehydration column was found to be 588 ppm by mass, and the steam ratio in the heavy ends column and the propionic acid concentration in the product were found respectively to be 1 and to be 160 ppm. The results are presented in Table 1. Other impurities in the reactor were found to typically include dimethyl ether, corrosion metals, organic carboxylic acids such as formic acid, alkanes, crotonaldehyde, 2-ethylcrotonaldehyde, and organic iodides such as ethyl iodide.

Comparative Example 2

An experiment was performed by a procedure similar to that in Comparative Example 1, except for charging methanol and carbon monoxide each in an amount half that in Comparative Example 1; lowering the reaction temperature, the rhodium catalyst concentration, and the methyl iodide concentration; and changing the liquid level only in the working reactor to 110, assuming that the corresponding liquid level in Comparative Example 1 is 100. As a result, acetic acid could not sufficiently evaporate in the subsequent flash step, and the operation became unstable. The results are presented in Table 1.

Comparative Example 3

An experiment was performed by a similar procedure to that in Comparative Example 1, except for charging methanol and carbon monoxide each in an amount half that in Comparative Example 1; and lowering the reaction temperature. As a result, the operation, which was performed at a reaction temperature of 170° C., was barely enough to allow acetic acid to evaporate and failed to produce acetic acid stably. The results are presented in Table 1.

Comparative Example 4

An experiment was performed by a procedure similar to that in Comparative Example 1, except for charging methanol and carbon monoxide each in an amount half that in Comparative Example 1; and changing the liquid level only in the working reactor to 120, assuming that the corresponding liquid level in Comparative Example 1 is 100. The results are presented in Table 1.

Comparative Example 5

An experiment was performed by a procedure similar to that in Comparative Example 1, except for charging methanol and carbon monoxide each in an amount half that in Comparative Example 1; and changing the liquid level only in the working evaporator to 120, assuming that the corresponding liquid level in Comparative Example 1 is 100. The results are presented in Table 1.

Comparative Example 6

An experiment was performed by a procedure similar to that in Comparative Example 1, except for charging methanol and carbon monoxide each in an amount half that in Comparative Example 1; and changing the liquid level of only the organic phase in the working decanter to 120, assuming that the corresponding liquid level in Comparative Example 1 is 100. The results are presented in Table 1.

Comparative Example 7

An experiment was performed by a procedure similar to that in Comparative Example 1, except for charging methanol and carbon monoxide each in an amount half that in Comparative Example 1; and changing the liquid levels in the working reactor and in the organic phase in the working decanter each to 120, assuming that the corresponding liquid levels in Comparative Example 1 are 100. The results are presented in Table 1.

Example 1

An experiment was performed by a procedure similar to that in Comparative Example 1, except for using two reactors in parallel (see FIG. 1), where each reactor had a capacity half that in Comparative Examples 1 and 2. As a result, the propionic acid concentration in the bottoms from the dehydration column was 586 ppm by mass, and the steam ratio in the heavy ends column was approximately the same as that in Comparative Example 1. The results are presented in Table 1.

Example 2

An experiment was performed by a procedure similar to that in Comparative Example 1 (or Example 1), except for operating one of the two parallel reactors, where each reactor had a capacity half as much as that in Comparative Examples 1 and 2. As a result, the propionic acid concentration in the bottoms from the dehydration column was 589 ppm by mass, and the steam ratio in the heavy ends column was approximately the same as those in Comparative Example 1 and Example 1. The results are presented in Table 1.

In Table 1, "CO" stands for carbon monoxide, "MeOH" stands for methanol, "LiI" stands for lithium iodide, "Rh" stands for a rhodium catalyst, "MeI" stands for methyl iodide, "PCO" stands for carbon monoxide partial pressure, "PH2" stands for hydrogen partial pressure, "STY" stands for space time yield, "AC" stands for acetic acid, and "PA" stands for propionic acid.

The amounts of methanol and carbon monoxide cannot be relatively compared. In terms of amount by mole, the amount of methanol by mole a value resulting from multiplying the amount of carbon monoxide by mole by 0.9 (namely, (amount of charged CO by mole)×0.9). The amount of acetic acid in the bottoms from the dehydration column is a value resulting from multiplying the amount of charged methanol by mole by 99.9% (namely, (amount of charge by mole)×99.9%).

TABLE 1

|  |  | Example 1 | Example 2 | Comp. Ex. 1 | Comp. Ex. 2 | Comp. Ex. 3 | Comp. Ex. 4 | Comp. Ex. 5 | Comp. Ex. 6 | Comp. Ex. 7 |
|---|---|---|---|---|---|---|---|---|---|---|
| Number of reactors provided | | 2 | 2 | 1 | 1 | 1 | 1 | 1 | 1 | 1 |
| Capacity per reactor | | 0.5 | 0.5 | 1 | 1 | 1 | 1 | 1 | 1 | 1 |
| Number of working reactors | | 2 | 1 | 1 | 1 | 1 | 1 | 1 | 1 | 1 |
| Total capacity of all reactors (in part) | | 0.5 × 2 = 1 | 0.5 × 1 = 0.5 | 1 | 1 | 1 | 1 | 1 | 1 | 1 |
| Reaction mixture in reactor(s) | CO in part by weight (*1) | 1 | 0.5 | 1 | 0.5 | 0.5 | 0.5 | 0.5 | 0.5 | 0.5 |
| | MeOH in part by weight (*1) | 1 | 0.5 | 1 | 0.5 | 0.5 | 0.5 | 0.5 | 0.5 | 0.5 |
| | Reaction temperature (° C.) | 187.9 | 188.1 | 188 | 180 | 170 | 188 | 179 | 178 | 188 |
| | Water (% by weight) | 2.0 | 2.0 | 2.0 | 2.0 | 2.0 | 2.0 | 2.0 | 2.0 | 2.0 |
| | AC (% by weight) | remainder | remainder | remainder | remainder | remainder | remainder | remainder | remainder | remainder |
| | Others (% by weight) | 0.8 | 0.9 | 0.9 | 0.8 | 0.9 | 0.7 | 0.8 | 0.9 | 0.8 |
| | LiI (% by weight) | 15.0 | 15.0 | 15.0 | 13.5 | 15.0 | 12.0 | 14.5 | 15.0 | 12.0 |
| | MA (% by weight) | 2.00 | 2.00 | 2.00 | 1.00 | 2.00 | 0.90 | 0.85 | 0.85 | 1.30 |
| | Rh (ppm by weight) | 902 | 898 | 899 | 809 | 899 | 719 | 791 | 899 | 719 |
| | MeI (% by weight) | 8.0 | 8.0 | 8.0 | 7.2 | 8.0 | 6.4 | 8.0 | 7.0 | 5.6 |
| | PCO (MPa) (absolute pressure) | 1.4 | 1.4 | 1.4 | 1.4 | 1.4 | 1.4 | 1.4 | 1.4 | 1.4 |
| | PH2 (MPa) (absolute pressure) | 0.07 | 0.07 | 0.07 | 0.08 | 0.05 | 0.08 | 0.09 | 0.1 | 0.06 |
| Variation in liquid level in reactor(s) in operation (*2) | | 100 | 100 | 100 | 110 | 100 | 120 | 100 | 100 | 120 |
| Variation in liquid level in working evaporator (*2) | | 100 | 100 | 100 | 100 | 100 | 100 | 120 | 100 | 100 |
| Variation in liquid level in working decanter (*2) | | 100 | 100 | 100 | 100 | 100 | 100 | 100 | 120 | 120 |
| Acetic acid STY (reaction rate) (*3) | | 100 | 100 | 100 | 50 | 50 | 50 | 50 | 50 | 50 |
| PA concentration in dehydration column bottoms (ppm by weight) | | 586 | 589 | 588 | 942 | 415 | 1062 | 1162 | 1152 | 667 |
| Steam ratio in heavy ends column (*4) | | 1.0 | 1.0 | 1.0 | 1.8 | 0.8 | 2.1 | 2.3 | 2.3 | 1.3 |
| PA concentration in product (ppm by weight) | | 158 | 155 | 160 | 162 | 160 | 162 | 163 | 161 | 161 |
| Acetic acid production volume (*3) | | 100 | 50 | 100 | 50 | 50 | 50 | 50 | 50 | 50 |

(*1) Value as determined assuming that the corresponding value in Comparative Example 1 is 1.

(*2) Values as determined assuming that the corresponding value in in Comparative Example 1 is 100 for the comparative examples; and values as determined assuming that the corresponding value in Example 1 is 100 for the examples.

(*3) Value as determined assuming that the corresponding value in Comparative Example 1 is 100.

(*4) The steam ratio in the heavy ends column was determined as the ratio of the steam amount to the acetic acid space time yield (SPY).

Discussion of Results

Comparative Examples 1 to 7 are operation examples using one reactor, and Examples 1 and 2 are operation examples using two parallel reactors.

Comparative Examples 1 and 2 are compared with each other. Comparative Example 2 is an operation example in which methanol and carbon monoxide were charged each in an amount half that in Comparative Example 1, and the reaction temperature, the rhodium catalyst concentration, and the methyl iodide concentration were lowered to lower the reaction rate. As a result, the propionic acid concentration in the bottoms from the dehydration column was very high, as high as 942 ppm. Therefore the product could not surely have a propionic acid concentration of 162 ppm unless the amount of steam used in the heavy ends column was increased to 1.8 parts. This demonstrates, in other words, that the purification requires a large amount of steam and requires much energy. However, such a significant reduction in reaction rate as to impede the reaction could be avoided in Comparative Example 2. This is because the liquid level in the working reactor was increased to 110, assuming that the corresponding liquid level in Comparative Example 1 is 100, and the rhodium catalyst concentration, the methyl iodide concentration, and the lithium iodide concentration could be lowered to some extent as compared with Comparative Example 1. However, reduction in load could not be avoided, and the methyl acetate concentration in the liquid reaction mixture was lowered as compared with Comparative Example 1. This caused increase in shift reaction to cause higher hydrogen partial pressure in the reactor. The reduction in methyl acetate concentration and the increase in hydrogen partial pressure in combination doubly affected and caused increase in propionic acid formation subsequent to acetaldehyde formation. Probably because of this, the propionic acid concentration in the bottoms from the dehydration column was increased up to about 2 times. In other words, the results demonstrate that a conventional acetic acid production method as in Comparative Example 2, when the acetic acid production volume is reduced to half, requires extra energy and cost to produce an acetic acid product with identical quality, because the method fails to significantly change the amounts of the catalyst and the promoter in the reaction system.

Comparative Example 3 is an example in which the liquid level adjustment was not performed, and the reaction temperature in the reactor was set to 170° C. As a result, acetic acid could not sufficiently evaporate in the subsequent flash step, and the operation became unstable. The hydrogen partial pressure in the reactor was lowered as compared with Comparative Example 1. These demonstrated that the technique of controlling the evaporation rate merely by lowering the reaction temperature adversely affects stable operation, and the conditions therein are not considered to be preferred production conditions.

Next, the results of Comparative Examples 2 and 4 to 7 will be discussed while focusing the effects of liquid level adjustment, which is the conventional technique.

Comparative Examples 2 and 4 are examples in which the liquid levels in the working reactor were raised respectively to 110 and 120, assuming that the corresponding liquid level in Comparative Example 1 is 100. As a result, as compared with Comparative Example 1, the rhodium catalyst concentrations, the methyl iodide concentrations, and the lithium iodide concentrations were lowered proportionally to the magnitude in liquid level increase. However, reduction in load could not be avoided. When the methyl acetate concentration in the liquid reaction mixture was lowered to about half that in Comparative Example 1 so as to adjust the acetic acid production volume, the shift reaction was increased to increase the hydrogen partial pressure in the reactor. The reduction in methyl acetate concentration and the increase in hydrogen partial pressure affected doubly in combination and caused increase in propionic acid formation subsequent to acetaldehyde formation. Therefore the product could not surely have a propionic acid concentration of 162 ppm unless the amount of steam used in the heavy ends column was increased to about 2 parts. In other words, the results demonstrate that the purification requires a large amount of steam and requires much energy.

Comparative Example 5 is an example in which the liquid level in the working evaporator was raised to 120, assuming that the corresponding liquid level in Comparative Example 1 is 100. As a result, the rhodium catalyst concentration and the lithium iodide concentration were lowered as compared with Comparative Example 1. However, reduction in load could not be avoided. When the methyl acetate concentration in the liquid reaction mixture was reduced to about half that in Comparative Example 1 so as to adjust the acetic acid production volume, the shift reaction was increased to increase the hydrogen partial pressure in the reactor. The reduction in methyl acetate concentration and the increase in hydrogen partial pressure affected doubly in combination and caused increase in propionic acid formation subsequent to acetaldehyde formation. Therefore, the product could not surely have a propionic acid concentration of 163 ppm unless the amount of steam used in the heavy ends column was increased to 2.3 parts. In other words, the results demonstrate that the purification requires a large amount of steam and requires much energy.

Comparative Example 6 is an example in which the liquid level of the organic phase (methyl iodide phase) in the working decanter was raised to 120, assuming that the corresponding liquid level in Comparative Example 1 is 100. As a result, the methyl iodide concentration in the liquid reaction mixture was lowered as compared with Comparative Example 1. However, reduction in load could not be avoided. When the methyl acetate concentration in the liquid reaction mixture was reduced to half that in Comparative Example 1 so as to adjust the acetic acid production volume, the shift reaction was increased to increase the hydrogen partial pressure in the reactor. The reduction in methyl acetate concentration and the increase in hydrogen partial pressure affected doubly in combination and caused increase in propionic acid formation subsequent to acetaldehyde formation. Therefore the product could not surely have a propionic acid concentration of 161 ppm unless the amount of steam used in the heavy ends column was increased to 2.3 parts. In other words, the results demonstrate that the purification requires a large amount of steam and requires much energy.

Comparative Example 7 is an example in which the liquid levels in the working reactor and in organic phase in the working decanter were each raised to 120, assuming that the corresponding liquid level in Comparative Example 1 is 100. As a result, the rhodium catalyst concentration, the methyl iodide concentration, and the lithium iodide concentration were lowered as compared with Comparative Example 1. However, reduction in load could not be avoided. To adjust the acetic acid production volume, the methyl acetate concentration in the liquid reaction mixture had to be lowered as compared with Comparative Example 1. The configuration caused increase in propionic acid formation, although the hydrogen partial pressure in the reactor did not significantly increase. Therefore, the product could not surely have a propionic acid concentration of 161 ppm unless the amount of steam used in the heavy ends column was increased to 1.3 parts. In other words, the results demonstrate that the purification requires much energy.

The results relating to the effects of the comparative examples as described above support as follows. In conventional or currently-employed plants according to a continuous process, only little advantageous effects are obtained even when the amounts of the metal catalyst and the promoter to be recycled into the reactor are adjusted by changing the amounts of starting material methanol and starting material carbon monoxide to be fed and by lowering the concentrations of the catalyst and the promoter in the reactor, or adjusting the reaction temperature, or raising the liquid level in the reactor, the evaporator, or the decanter. The results also demonstrate that the conventional technique requires extra energy and cost and gives disadvantages rather than advantages when production is performed by operating regular plant facilities without modification and reducing the acetic acid production volume alone to half that in regular or general operation.

In contrast, Examples 1 and 2 gave results in the propionic acid concentration in the bottoms from the dehydration column and the steam ratio at the heavy ends column, equivalent to those in Comparative Example 1, which is an operation example according to the conventional technique. Namely, the results demonstrate that Examples 1 and 2 enable efficient production, with easy, simple operation, of acetic acid having quality equivalent to that in the conventional technique.

Examples 1 and 2 are compared with each other. Examples 1 and 2 are identical in employing two reactors in parallel, but different in the number (2 or 1) of working reactors. These examples were evaluated for variations in metal catalyst (rhodium catalyst) concentration, methyl iodide concentration, iodide salt concentration, acetic acid concentration, water concentration, methyl acetate concentration, hydrogen partial pressure, and reaction temperature, in the reactor. The results demonstrate that there are no or very little variations due to change in number of reactors in operation, and that these examples are identical in acetic acid reaction rate.

These results demonstrate as follows. The acetic acid production method according to the present invention, which method employs two or more reactors in parallel in the carbonylation step, enables smooth reduction and/or increase of acetic acid production with easy operation and enables industrially efficient, stable production of acetic acid with maintained quality even when the acetic acid production volume is changed. In addition, the method allows the concentrations of components in the reaction mixture, reaction temperature, and hydrogen partial pressure in the reactor to be held constant without large variations, regardless of the number of reactors in operation.

The results also demonstrate that, with the acetic acid production method according to the present invention, the liquid levels in the reactor(s) in operation, the working evaporator, and the working decanter are held constant without variations, regardless of the number of reactors in operation.

The results also demonstrate that, with the acetic acid production method according to the present invention, the acetic acid space time yield in the carbonylation step is held constant even when the acetic acid production volume is reduced down to 50%.

As a summary of the above description, the configurations according to embodiments of the present invention, as well as variations thereof, will be listed below as appendices.

(1) A method for producing acetic acid, the method including a carbonylation step of reacting methanol with carbon monoxide in a continuous system in the presence of a catalytic system, acetic acid, methyl acetate, and water, the catalytic system including a metal catalyst and methyl iodide, the carbonylation step employing two or more reactors disposed in parallel.

(2) The acetic acid production method according to (1), wherein the method further includes, in addition to the carbonylation step, an evaporation step of separating, using an evaporator, a reaction mixture from the carbonylation step into a vapor stream and a residue stream, and wherein the evaporator includes two or more evaporators disposed in parallel and coupled respectively to the two or more parallel reactors.

(3) The acetic acid production method according to one of (1) and (2), wherein the method further includes, in addition to the carbonylation step:

an evaporation step of separating, using an evaporator, a reaction mixture from the carbonylation step into a vapor stream and a residue stream; and a light ends-removing step of separating, by distillation using a distillation column, the vapor stream into an overhead stream rich in at least one light end selected from methyl iodide and acetaldehyde, and an acetic acid stream rich in acetic acid, and subjecting the overhead stream sequentially to condensation and to liquid-liquid separation using a decanter to give an aqueous phase and an organic phase, and wherein the evaporator includes two or more evaporators disposed in parallel and coupled respectively to the two or more parallel evaporators, and the distillation column includes two or more distillation columns disposed in parallel and coupled respectively to the two or more parallel evaporators.

(4) The acetic acid production method according to any one of (1) to (3), wherein the acetic acid production volume is increased or decreased by increasing or decreasing the number of reactors in operation, of the two or more parallel reactors.

(5) The acetic acid production method according to any one of (1) to (4), wherein, during operation with increase or decrease in number of reactors in operation, the reactor(s) in operation is operated at a reaction temperature of 170° C. or higher, and at least one of conditions (i) to (vii) is met regardless of the number of reactors in operation, where the conditions (i) to (vii) are expressed as follows:

(i) variations in metal catalyst concentration and methyl iodide concentration in the reactor(s) in operation fall within ±50%;

(ii) the catalytic system further includes an iodide salt, and a variation in iodide salt concentration in the reactor(s) in operation falls within ±50%;

(iii) a variation in reaction temperature in the reactor(s) in operation falls within ±20° C.;

(iv) a variation in at least one of acetic acid concentration, methyl acetate concentration, and water concentration in the reactor(s) in operation falls within ±50%;

(v) a variation in hydrogen partial pressure in the reactor(s) in operation falls within ±50%;

(vi) a variation in reaction rate in the reactor(s) in operation falls within ±50%; and (vii) a variation in acetic acid space time yield in the reactor(s) in operation falls within ±40%.

(6) The acetic acid production method according to (5), wherein, relating to the condition (i), the variation in metal catalyst concentration in the reactor(s) in operation falls within ±40% (preferably within ±30%, more preferably within ±20%, furthermore preferably within ±10%, and particularly preferably within ±5%).

(7) The acetic acid production method according to one of (5) and (6), wherein, relating to the condition (1), the variation in methyl iodide concentration in the reactor(s) in operation falls within ±40% (preferably within ±30%, more preferably within ±20%, furthermore preferably within ±10%, and particularly preferably within ±5%).

(8) The acetic acid production method according to any one of (5) to (7), wherein, relating to the condition (ii), the variation in iodide salt concentration in the reactor(s) in operation falls within ±40% (preferably within ±30%, more preferably within ±20%, furthermore preferably within ±10%, and particularly preferably within ±5%).

(9) The acetic acid production method according to any one of (5) to (8), wherein, relating to the condition (iii), the variation in reaction temperature in the reactor(s) in operation falls within ±15° C. (preferably within ±10° C., more preferably within ±8° C., furthermore preferably within ±5° C., and particularly preferably within ±3° C.)

(10) The acetic acid production method according to any one of (5) to (9), wherein, relating to the condition (iv), the variation in acetic acid concentration in the reactor(s) in operation falls within ±40% (preferably within ±30%, more preferably within ±20%, furthermore preferably within ±10%, and particularly preferably within ±5%).

(11) The acetic acid production method according to any one of (5) to (10), wherein, relating to the condition (iv), the variation in methyl acetate concentration in the reactor(s) in operation falls within ±40% (preferably within ±30%, more preferably within ±20%, furthermore preferably within ±10%, and particularly preferably within ±5%).

(12) The acetic acid production method according to any one of (5) to (11), wherein, relating to the condition (iv), the variation in water concentration in the reactor(s) in operation falls within ±40% (preferably within ±30%, more preferably within ±20%, furthermore preferably within ±10%, and particularly preferably within ±5%).

(13) The acetic acid production method according to any one of (5) to (12), wherein, relating to the condition (v), the variation in hydrogen partial pressure in the reactor(s) in operation falls within ±40% (preferably within ±30%, more preferably within ±20%, furthermore preferably within ±10%, and particularly preferably within ±5%).

(14) The acetic acid production method according to any one of (5) to (13), wherein, relating to the condition (vi), the variation in reaction rate in the reactor(s) in operation falls within ±40% (preferably within ±30%, more preferably within ±20%, furthermore preferably within ±10%, and particularly preferably within ±5%).

(15) The acetic acid production method according to any one of (5) to (14), wherein, relating to the condition (vii), the variation in acetic acid space time yield (also called "acetic acid formation rate") in the reactor(s) in operation falls within ±35% (e.g., within ±30%, within ±25%, within ±20%, preferably within ±15%, more preferably within ±10%, furthermore preferably within ±8%, particularly preferably within ±5%, and especially preferably within ±3%).

(16) The acetic acid production method according to any one of (5) to (15), wherein at least one of the conditions (i) to (vii) is met between before and after switchover to increase or decrease in number of reactors in operation.

(17) The acetic acid production method according to any one of (5) to (16), wherein at least the conditions (i), (ii), and (iii) are met together between before and after switchover to increase or decrease in number of reactors in operation.

(18) The acetic acid production method according to any one of (5) to (17), wherein at least the conditions (i), (ii), (iii), and (iv) are met together between before and after switchover to increase or decrease in number of reactors in operation.

(19) The acetic acid production method according to any one of (5) to (18), wherein at least the conditions (1), (ii), (iii), (iv), and (v) are met together between before and after switchover to increase or decrease in number of reactors in operation.

(20) The acetic acid production method according to any one of (5) to (19), wherein at least the conditions (i), (ii), (iii), (iv), (v), and (vi) are met together between before and after switchover to increase or decrease in number of reactors in operation.

(21) The acetic acid production method according to any one of (5) to (20), wherein all the conditions (i), (ii), (iii), (iv), (v), (vi), and (vii) are met together between before and after switchover to increase or decrease in number of working reactor.

(22) The acetic acid production method according to any one of (1) to (21),
wherein the method further includes, in addition to the carbonylation step, an evaporation step of separating, using an evaporator, a reaction mixture from the carbonylation step into a vapor stream and a residue stream, and
wherein a liquid volume in the evaporator is 1 to 100 parts by volume (e.g., 1 to 70 parts by volume, preferably 1 to 50 parts by volume, more preferably 1 to 30 parts by volume, furthermore preferably 1 to 20 parts by volume, and particularly preferably 1 to 10 parts by volume) per 100 parts by volume of the total liquid volume in the parallel reactors, where, when the evaporator includes two or more evaporators disposed in parallel, the term "liquid volume in the evaporator" is read as "total liquid volume in the two or more evaporators".

(23) The acetic acid production method according to any one of (1) to (22), wherein the method further includes, in addition to the carbonylation step:
an evaporation step of separating, using an evaporator, a reaction mixture from the carbonylation step into a vapor stream and a residue stream; and
a light ends-removing step of separating, by distillation using a distillation column, the vapor stream into an overhead stream rich in at least one light end selected from methyl iodide and acetaldehyde, and an acetic acid stream rich in acetic acid, and subjecting the overhead stream sequentially to condensation and to liquid-liquid separation using a decanter, to give an aqueous phase and an organic phase, and
wherein a liquid volume in the decanter is 1 to 100 parts by volume (e.g., 1 to 70 parts by volume, preferably 1 to 50 parts by volume, more preferably 1 to 30 parts by volume, furthermore preferably 1 to 20 parts by volume, and particularly preferably 1 to 10 parts by volume) per 100 parts by volume of the total liquid volume in the parallel reactors, where, when the decanter includes two or more decanters disposed in parallel, the term "liquid volume in the decanter" is read as "total liquid volume in the two or more decanters".

(24) The acetic acid production method according to any one of (1) to (23), wherein the method further includes, in addition to the carbonylation step:

an evaporation step of separating, using an evaporator or evaporators, a reaction mixture from the carbonylation step into a vapor stream and a residue stream; and a light ends-removing step of separating, by distillation, the vapor stream into an overhead stream rich in at least one light end selected from methyl iodide and acetaldehyde, and an acetic acid stream rich in acetic acid, and subjecting the overhead stream sequentially to condensation and to liquid-liquid separation using a decanter or decanters, to give an aqueous phase and an organic phase, and wherein, during operation with increase or decrease in number of reactors in operation, the reactor(s) in operation is operated at a reaction temperature of 170° C. or higher, and at least one of conditions (viii) to (x) is met regardless of the number of reactors in operation, where the conditions (viii) to (x) are expressed as follows:

(viii) a variation in liquid level in the reactor(s) in operation falls within ±20%;

(ix) a variation in liquid level in the working evaporator(s) falls within ±20%; and (x) a variation in liquid level in the working decanter(s) falls within ±20%.

(25) The acetic acid production method according to (24), wherein, relating to the condition (viii), the variation in liquid level in the reactor(s) in operation falls within ±15% (preferably within ±10%, more preferably within ±8%, furthermore preferably within ±5%, and particularly preferably within ±3%).

(26) The acetic acid production method according to one of (24) and (25), wherein, relating to the condition (ix), the variation in liquid level in a working evaporator falls within ±15% (preferably within ±10%, more preferably within ±8%, furthermore preferably within ±5%, and particularly preferably within ±3%).

(27) The acetic acid production method according to any one of (24) to (26), wherein, relating to the condition (x), the variation in liquid level in a working decanter falls within ±15% (preferably within ±10%, more preferably within ±8%, furthermore preferably within ±5%, and particularly preferably within ±3%).

(28) The acetic acid production method according to any one of (24) to (27), wherein at least one of the conditions (viii) to (x) is met between before and after switchover to increase or decrease in number of reactors in operation.

(29) The acetic acid production method according to any one of (24) to (28), wherein at least one of the conditions (viii) and (ix) are met together between before and after switchover to increase or decrease in number of reactors in operation.

(30) The acetic acid production method according to any one of (24) to (29), wherein all the conditions (viii), (ix), and (x) are met together between before and after switchover to increase or decrease in number of reactors in operation.

(31) A method for producing acetic acid, the method including a carbonylation step or reacting methanol with carbon monoxide in a continuous system in the presence of a catalytic system, acetic acid, methyl acetate, and water, where the catalytic system includes a metal catalyst and methyl iodide, wherein a variation in acetic acid space time yield in the carbonylation step is held within ±40% (e.g., within ±35%, within ±30%, within ±25%, within ±20%, preferably within ±15%, more preferably within ±10%, furthermore preferably within ±8%, and particularly preferably within ±5%, and especially preferably within ±3), upon reduction in acetic acid production volume to 30% to 90% (e.g., 35%, 40%, 45%, 50%, 55%, 60%, 65%, 70%, 75%, 80%, or 85%).

(32) The acetic acid production method according to (30), wherein the carbonylation step employs two or more parallel reactors, and wherein the acetic acid production volume is reduced by decreasing the number of reactors in operation.

INDUSTRIAL APPLICABILITY

The acetic acid production methods according to embodiments of the present invention are applicable as methods for industrially producing acetic acid by the methanol carbonylation process (methanol-acetic acid process).

REFERENCE SIGNS LIST 1A, 1B reactor
2A, 2B evaporator
3A, 3B, 5, 6, 10 distillation column
4 decanter
7 ion exchange resin column
8 scrubbing system
9 acetaldehyde-removing system
16 reaction mixture feed line
17 vapor stream discharge line
18, 19 residue stream recycle line
54 carbon monoxide-containing gas inlet line
55, 56 potassium hydroxide inlet line
57 catalyst circulating pump

The invention claimed is:

1. A method for producing acetic acid, the method comprising:

a carbonylation step of reacting methanol with carbon monoxide in a continuous system in the presence of a catalytic system, acetic acid, methyl acetate, and water, wherein the catalytic system comprises a metal catalyst and methyl iodide;

wherein the carbonylation step employs two or more reactors disposed in parallel;

an evaporation step of separating, in an evaporator, a reaction mixture from the carbonylation step into:
a vapor stream, and
a residue stream; and a light ends-removing step of:
separating, by distillation in a first distillation column, the vapor stream into:
an overhead stream rich in at least one light end selected from methyl iodide and acetaldehyde, and
an acetic acid stream rich in acetic acid; and
subjecting the overhead stream sequentially to condensation and to a liquid-liquid separation in a decanter, to form:
an aqueous phase, and
an organic phase;

wherein, in the evaporation step, the residue stream is recycled to the two or more parallel reactors;

wherein an acetic acid production volume is increased or decreased by increasing or decreasing the number of reactors in operation of the two or more parallel reactors;

wherein the reactor or reactors are each operated where at least one of following conditions (a) to (c) is met:
(a) two or more reactors are used in parallel, and only one evaporator is used;

(b) the evaporator includes two or more evaporators disposed in parallel and coupled respectively to the two or more parallel reactors, and only one first distillation column is used; and
(c) the method comprising a dehydration step of subjecting the acetic acid stream from the light ends-removing step to a distillation treatment in a second distillation column so as to further purify acetic acid, wherein
the evaporator comprises two or more evaporators disposed in parallel and coupled respectively to the two or more parallel reactors;
the first distillation column comprises two or more distillation columns disposed in parallel and coupled respectively to the two or more parallel evaporators; and
only one second distillation column is used;
wherein, during operation with an increase or decrease in number of reactors in operation, the reactor or reactors in operation are each operated at a reaction temperature of 170° C. or higher, the following conditions (i) and (iii) are met regardless of the number of reactors, and at least one of following conditions (ii) and (iv)-(vii) is met regardless of the number of reactors in operation, where the conditions (i) to (vii) are expressed as follows:
(i) variations in metal catalyst concentration and methyl iodide concentration in the reactor or reactors in operation fall within ±50%;
(ii) the catalytic system further includes an iodide salt, and a variation in iodide salt concentration in the reactor or reactors in operation falls within ±50%;
(iii) a variation in reaction temperature in the reactor or reactors in operation falls within ±20° C.;
(iv) a variation in at least one of acetic acid concentration, methyl acetate concentration, and water concentration in the reactor or reactors in operation falls within ±50%;
(v) a variation in hydrogen partial pressure in the reactor or reactors in operation falls within ±50%;
(vi) a variation in reaction rate in the reactor or reactors in operation falls within ±50%; and
(vii) a variation in acetic acid space time yield in the reactor or reactors in operation falls within ±40%.

2. The acetic acid production method according to claim 1,
wherein at least one of the conditions (i) to (vii) is met between before and after switchover to increase or decrease in number of reactors in operation.

3. The acetic acid production method according to claim 1,
wherein the method further comprises, in addition to the carbonylation step,
wherein a liquid volume in the evaporator is 1 to 100 parts by volume per 100 parts by volume of the total liquid volume in the parallel reactors, where, when the evaporator comprises two or more evaporators disposed in parallel, said liquid volume in the evaporator is a total liquid volume in the two or more evaporators.

4. The acetic acid production method according to claim 1,
wherein a liquid volume in the decanter is 1 to 100 parts by volume per 100 parts by volume of the total liquid volume in the parallel reactors, where, when the decanter includes two or more decanters disposed in parallel, said liquid volume in the decanter is a total liquid volume in the two or more decanters.

5. The acetic acid production method according to claim 1,
wherein, during operation with increase or decrease in number of reactors in operation,
at least one of conditions (viii) to (x) is met regardless of the number of operating reactors, where the conditions (viii) to (x) are expressed as follows:
(viii) a variation in liquid level in the reactor or reactors in operation falls within ±20%;
(ix) a variation in liquid level in the working evaporator or evaporators falls within ±20%; and
(x) a variation in liquid level in the working decanter or decanters falls within ±20%.

6. A method for producing acetic acid, the method comprising:
a carbonylation step of reacting methanol with carbon monoxide in a continuous system in the presence of a catalytic system, acetic acid, methyl acetate, and water, the catalytic system including a metal catalyst and methyl iodide,
an evaporation step of separating, in an evaporator, a reaction mixture from the carbonylation step into:
a vapor stream, and
a residue stream; and
a light ends-removing step of:
separating, by distillation in a first distillation column, the vapor stream into:
an overhead stream rich in at least one light end selected from methyl iodide and acetaldehyde, and
an acetic acid stream rich in acetic acid; and
subjecting the overhead stream sequentially to condensation and to a liquid-liquid separation in a decanter, to form:
an aqueous phase, and
an organic phase;
wherein, in the evaporation step, the residue stream is recycled to the two or more parallel reactors;
wherein the reactor or reactors are each operated where at least one of following conditions (a) to (c) is met:
(a) two or more reactors are used in parallel, and only one evaporator is used;
(b) the evaporator includes two or more evaporators disposed in parallel and coupled respectively to the two or more parallel reactors, and only one first distillation column is used; and
(c) the method comprising a dehydration step of subjecting the acetic acid stream from the light ends-removing step to a distillation treatment in a second distillation column so as to further purify acetic acid, wherein
the evaporator comprises two or more evaporators disposed in parallel and coupled respectively to the two or more parallel reactors;
the first distillation column comprises two or more distillation columns disposed in parallel and coupled respectively to the two or more parallel evaporators; and
only one second distillation column is used;
wherein a variation in acetic acid space time yield in the carbonylation step is held within ±40% when an acetic acid production volume is reduced down to a range of from 30% to 90%,
wherein the carbonylation step employs two or more reactors disposed in parallel,
wherein the acetic acid production volume is reduced by decreasing the number of reactors in operation, and wherein the following conditions are met regardless of the number of reactors in operation:
variations in metal catalyst concentration and methyl iodide concentration in the reactor or reactors in operation fall within ±50%; and
a variation in reaction temperature in the reactor or reactors in operation falls within ±20° C.

* * * * *